United States Patent
Itu et al.

(10) Patent No.: US 10,483,006 B2
(45) Date of Patent: Nov. 19, 2019

(54) LEARNING BASED METHODS FOR PERSONALIZED ASSESSMENT, LONG-TERM PREDICTION AND MANAGEMENT OF ATHEROSCLEROSIS

(71) Applicant: Siemens Healthcare GmbH, Erlangen (DE)

(72) Inventors: Lucian Mihai Itu, Brasov (RO); Tiziano Passerini, Plainsboro, NJ (US); Saikiran Rapaka, Pennington, NJ (US); Puneet Sharma, Manmouth Junction, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 40 days.

(21) Appl. No.: 15/599,505

(22) Filed: May 19, 2017

(65) Prior Publication Data
US 2018/0336319 A1 Nov. 22, 2018

(51) Int. Cl.
  *G16H 50/70* (2018.01)
  *G16B 25/00* (2019.01)
(52) U.S. Cl.
  CPC .......... *G16H 50/70* (2018.01); *G16B 25/00* (2019.02); *G01N 2800/323* (2013.01)
(58) Field of Classification Search
  CPC .......... H04W 72/0406; H04W 24/02; H04W 72/0413; H04W 88/08; H04W 88/02; H04W 52/365; H04L 41/0803; H04L 61/6022
  See application file for complete search history.

(56) References Cited

U.S. PATENT DOCUMENTS

| | | | | |
|---|---|---|---|---|
| 2003/0199767 A1* | 10/2003 | Cespedes | ........ | A61B 5/01 600/473 |
| 2009/0299175 A1* | 12/2009 | Bernstein | ........ | A61B 5/05 600/425 |
| 2015/0032474 A1* | 1/2015 | Dobrean | ........ | G06Q 10/10 705/3 |
| 2015/0065846 A1* | 3/2015 | Choi | ........ | A61B 5/02007 600/407 |
| 2016/0066861 A1* | 3/2016 | Taylor | ........ | A61B 5/7275 600/485 |

(Continued)

FOREIGN PATENT DOCUMENTS

| | | |
|---|---|---|
| WO | 2015058044 A1 | 4/2015 |
| WO | 2016075331 A2 | 5/2016 |

OTHER PUBLICATIONS

Figueroa et al. "A computational framework for fluid-solid-growth modeling in cardiovascular simulations", Comput. Methods Appl. Mech. Engrg. 198 (2009) 3583-3602 (Year: 2009).*

(Continued)

*Primary Examiner* — Qian Yang

(57) ABSTRACT

A computer-implemented method for providing a personalized evaluation of assessment of atherosclerotic plaques for a patient acquiring patient data comprising non-invasive patient data, medical images of the patient, and blood biomarkers. Features of interest are extracted from the patient data and one or more machine learning models are applied to the features of interest to predict one or more measures of interest related to atherosclerotic plaque.

16 Claims, 21 Drawing Sheets

(56) References Cited

U.S. PATENT DOCUMENTS

| | | |
|---|---|---|
| 2016/0148371 A1 | 5/2016 | Itu et al. |
| 2016/0310018 A1 | 10/2016 | Fonte et al. |
| 2017/0018081 A1 | 1/2017 | Taylor et al. |

OTHER PUBLICATIONS

[Chatzizisis et al., 2007] Role of endothelial shear stress in the natural history of coronary atherosclerosis and vascular remodeling: molecular, cellular, and vascular behavior. J Am Coll Cardiol 49: 2379-93, 2007.
[Corban et al., 2014] Combination of plaque burden, wall shear stress, and plaque phenotype has incremental value for prediction of coronary atherosclerotic plaque progression and vulnerability. Atherosclerosis 232:271-6, 2014.
[Toutouzas et al., 2015] Accurate and reproducible reconstruction of coronary arteries and endothelial shear stress calculation using 3D OCT: comparative study to 3D IVUS and 3D QCA. Atherosclerosis 240: 510-9, 2015.
[Stone et al., 2012] Prediction of progression of coronary artery disease and clinical outcomes using vascular profiling of endothelial shear stress and arterial plaque characteristics: the Prediction Study. Circulation 126: 172-81, 2012.
[Slager et al., 2005] The role of shear stress in the destabilization of vulnerable plaques and related therapeutic implications. Nat Clin Pract Cardiovasc Med 2: 456-64, 2005.
[Glagov et al., 1988] Hemodynamics and atherosclerosis. Insights and perspectives gained from studies of human arteries. Arch Pathol Lab Med 1988; 112: 1018-1031.
[Yla-Herttuala et al., 2013] Stabilisation of atherosclerotic plaques: An update. Eur Heart J 2013; 34: 3251-3258.
[Cheng et al., 2006] Atherosclerotic lesion size and vulnerability are determined by patterns of fluid shear stress. Circulation 2006; 113: 2744-2753.
[Glagov et al., 1987] Compensatory enlargement of human atherosclerotic coronary arteries. N Engl J Med 1987; 316: 1371-1375.
[Cicha et al., 2011] Carotid plaque vulnerability: A positive feedback between hemodynamic and biochemical mechanisms. Stroke 2011; 42: 3502-3510.
[Gijsen et al., 2014] 3D reconstruction techniques of human coronary bifurcations for shear stress computations. J Biomech 2014; 47: 39-43.
[Assemat et al., 2013] Evolution and rupture of vulnerable plaques: a review of mechanical effects, ChronoPhysiology and Therapy, vol. 2013:3 pp. 23-40, 2013.
[Cibis et al., 2014] Wall shear stress calculations based on 3D cine phase contrast MRI and computational fluid dynamics: a comparison study in healthy carotid arteries. NMR Biomed 2014; 27: 826-834.
[Ku et al., 1985] Pulsatile flow and atherosclerosis in the human carotid bifurcation. Positive correlation between plaque location and low oscillating shear stress. Arteriosclerosis. 1985;5:293-302.
[Thim et al., 2012] Wall shear stress and local plaque development in stenosed carotid arteries of hypercholesterolemic minipigs. J Cardiovasc Dis Res. 2012;3:76-83.
[Depaolo et al., 1991] Vascular endothelium responds to fluid shear stress gradients. Arterioscler Thromb. 1991;12:1254-1257.
[Kulcsar et al., 2011] Hemodynamics of cerebral aneurysm initiation: the role of wall shear stress and spatial wall shear stress gradient. AJNR Am J Neuroradiol 32: 587-94, 2011.
[Tanoue et al., 2011] Wall shear stress distribution inside growing cerebral aneurysm. AJNR Am J Neuroradiol 32:1732-7, 2011.
[Hashimoto et al., 2006] Intracranial aneurysm: link among inflammation, hemodynamics and vascular remodeling. Neurol Res 28: 372-80, 2006.
[Ma et al., 2004] Three-dimensional geometrical characterization of cerebral aneurysms. Ann Biomed Eng 32: 264-73, 2004.

[Cebral et al., 2005] Characterization of cerebral aneurysms for assessing risk of rupture by using patient-specific computational hemodynamics models AJNR Am J Neuroradiol 26: 2550-59, 2005.
[Davis et al., 1993] Mechanical stress mechanisms and the cell: an endothelial paradigm. Circ Res 72: 239-45, 1993.
[Li et al., 2005] Molecular basis of the effects of shear stress on vascular endothelial cells. J Biomech 38: 1949-71, 2005.
[Jou et al., 2008] Wall shear stress on ruptured and unruptured intracranial aneurysms at the internal carotid artery. AJNR Am J Neuroradiol 29:1761-7, 2008.
[Dobrin et al., 1978] Mechanical properties of arteries. Physiol Rev. 1978;58: 397-460.
[Taylor et al., 2013] Computational fluid dynamics applied to cardiac computed tomography for noninvasive quantification of fractional flow reserve: scientific basis. J Am Coll Cardiol 61: 2233-2241,2013.
[Topoleski et al., 2000] Mechanical behaviour of calcified plaques: a summary of compression and stress-relaxation experiments. Z Kardiol. 2000;89 Suppl 2:85-91.
[Loree et al., 1994] Static circumferential tangential modulus of human atherosclerotic tissue. J Biomech. 1994;27:195-204.
[Lee et al., 2008] Geometry of the carotid bifurcation predicts its exposure to disturbed flow. Stroke 2008; 39: 2341-2347.
[Thomas et al., 2005] Variation in the carotid bifurcation geometry of young versus older adults: implications for geometric risk of atherosclerosis. Stroke 2005; 36: 2450-2456.
[Perktold et al., 1991] Pulsatile non-Newtonian blood flow in three-dimensional carotid bifurcation models: a numerical study of flow phenomena under different bifurcation angles. J Biomed Eng 1991; 13: 507-515.
[Schmidhuber, 2015] Deep learning in neural networks: an overview, Neural Networks 61: 85-117, 2015.
[Huang et al., 2015] Online Tensor Methods for Learning Latent Variable Models, Journal of Machine Learning Research 16 (2015) 2797-2835.
[Stoudenmire et al., 2016] Supervised Learning with Quantum-Inspired Tensor Networks, https://arxiv.org/abs/1605.05775, 2016.
[Yu et al., 2013] The Deep Tensor Neural Network With Applications to Large Vocabulary Speech Recognition, IEEE Transactions on Audio, Speech, and Language Processing, vol. 21, 2013.
[Diehn et al., 2008] Identification of noninvasive imaging surrogates for brain tumor gene-expression modules, National Academy of Sciences, 105 (13): 5213-8, 2008.
[Mazurowski, 2015] Radiogenomics: what it is and why it is important, J Am Coll Radiol. Aug. 2015;12(8):862-6.
[McLean et al., 2012] Cardiac biomarkers in the intensive care unit, Annals of Intensive Care 2012, 2:8.
[Bourantas et al., 2013] Early detection and invasive passivation of future culprit lesions: a future potential or an unrealistic pursuit of chimeras?. Am Heart J 165: 869-881, 2013.
[Serruys et al., 2012] From metallic cages to transient bioresorbable scaffolds: change in paradigm of coronary revascularization in the upcoming decade? Eur Heart J 33: 16-25, 2012.
[Pellionisz et al., 1985] Tensor network theory of the meta organization of functional geometries in the central nervous system,Neuroscience, vol. 16, pp. 245-273, 1985.
[Deng, 2014] A tutorial survey of architectures, algorithms, and applications for deep learning, APSIPA Transactions on Signal and Information Processing, vol. 3, 2014.
[Brunton et al., 2016] Discovering governing equations from data by sparse identification of nonlinear dynamical systems, PNAS, pp. 3932-3937, 2016.
[Parish et al., 2016] A paradigm for data-driven predictive modeling using field inversion and machine learning, Journal of Computational Physics, vol. 305, Jan. 15, 2016, pp. 758-774.
[Redgrave et al., 2008] Critical cap thickness and rupture in symptomatic carotid plaques: the Oxford Plaque Study. Stroke. 2008;39:1722-1729.
Amodio G, Antonelli G, Di Serio F. Cardiac biomarkers in acute coronary syndromes: a review. Curr Vasc Pharmacol. May 2010;8(3):388-93.
David Del Val Martin, et al, Biomarkers in acute coronary syndrome, IJC Metabolic & Endocrine vol. 8, Sep. 2015, pp. 20-23.

(56) References Cited

OTHER PUBLICATIONS

Soudah et al. CFD Modelling of Abdominal Aortic Aneurysm on Hemodynamic Loads Using a Realistic Geometry with CT Hindawi Publishing Corporation; Computational and Mathematical Methods in Medicine; vol. 2013, Article ID 472564, 9 pages.
Gijsen, Frank J.H. et al.: "3D reconstruction techniques of human coronary bifurcations for shear stress computations"; in: Journal of Biomechanics; pp. 1-5; 2013.
Extended European Search Report (EESR) dated Oct. 15, 2018 in corresponding European Patent Application No. 18172539.1.

\* cited by examiner

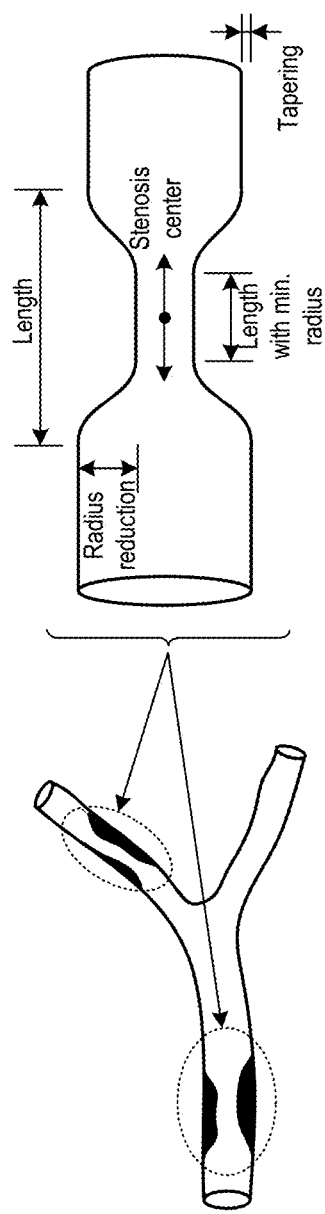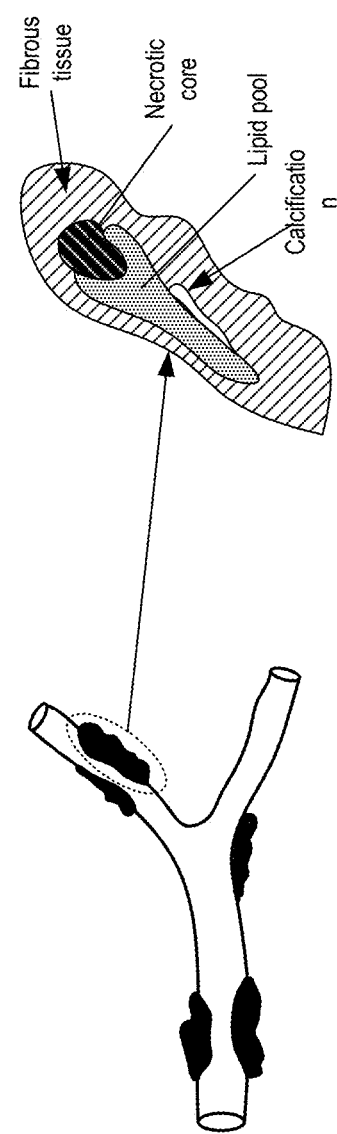
Fig. 4D
Fig. 4E

LEARNING BASED METHODS FOR PERSONALIZED ASSESSMENT, LONG-TERM PREDICTION AND MANAGEMENT OF ATHEROSCLEROSIS

TECHNICAL FIELD

The present invention relates generally to methods, systems, and apparatuses for the personalized evaluation of atherosclerotic plaques using machine-learning techniques.

BACKGROUND

Cardiovascular disease (CVD) is the leading cause of death, globally. The most prevalent and devastating CVD is atherosclerosis, a chronic, inflammatory, fibroproliferative disorder primarily of large- and medium-sized conduit arteries. Its initiation and progression is closely linked to the vascular endothelium, which responds to the dynamic forces acting on the vessel wall because of the complex geometry of the arteries, and the acquired presence of pathologic characteristics such as atherosclerotic plaque.

The majority of cardiovascular events, like stroke and myocardial infarction, are caused by atherosclerotic plaque ruptures, which cause distal embolization. Previous studies have shown that hemodynamic quantities are linked to the initiation, progression and rupture of atherosclerotic plaques. These hemodynamic quantities are in turn influenced both by systemic properties and the local geometry (certain regions, like bifurcations are predisposed to plaque formation). Thus, hemodynamic quantities, i.e. pressure, velocities, flow rate and flow-generated endothelial shear stresses (ESS), play a crucial role in the understanding of plaque initiation, progression, and rupture. Further, a combination of hemodynamic factors with other patient information (like demographics, blood biomarker information, past history, etc.) can be used to obtain a coherent understanding of the patient's condition as well as better understanding of patient outcomes.

SUMMARY

Embodiments of the present invention address and overcome one or more of the above shortcomings and drawbacks by providing methods, systems, and apparatuses related to the personalized assessment of atherosclerotic plaque using machine-learning techniques.

According to some embodiments, a computer-implemented method for providing a personalized evaluation of assessment of atherosclerotic plaques for a patient acquiring patient data comprising non-invasive patient data, medical images of the patient, and blood biomarkers. Features of interest are extracted from the patient data and one or more machine learning models are applied to the features of interest to predict one or more measures of interest related to atherosclerotic plaque. In some embodiments, a report is generated in a structured format describing the measures of interest related to atherosclerotic plaque. This report may be stored in a patient-specific medical record.

In some embodiments of the aforementioned method, the machine learning models are trained using a database of synthetic data comprising one or more of in silico anatomical models and in vitro anatomical models. The machine learning models may be trained by first performing fluid solid growth (FSG) computations for the in silico anatomical models or flow experiments for the in vitro anatomical models to yield output data. Measures of interest are extracted from the output data, and geometric features and plaque-related features are extracted from the database of synthetic data. Then, the machine learning models are trained to predict measures of interest related to atherosclerotic plaque using the measures of interest from the output data, the geometric features, and the plaque-related features.

The in silico anatomical models may be generated by initializing a new in silico anatomical model skeleton of a coronary arterial tree anatomical model by prescribing a number of vessels at each generation of the coronary arterial tree and defining healthy geometric information for each generation of the coronary arterial tree. The healthy geometric information comprises one or more of vessel radius, a degree of tapering, and a branch length. Stenoses in the coronary arterial tree may then be established which modify the healthy geometric information. Additionally, plaque composition may be established for each stenosis in the coronary arterial tree. Next, the new in silico anatomical model is updated based on the modified healthy geometric information and the plaque composition for each stenosis in the coronary arterial tree. Once updated, the new in silico anatomical model is stored in the database of synthetic data.

In some embodiments, the plaque composition for each stenosis may be established by randomly selecting a particular plaque composition from a plurality of predefined plaque composition types. For example, in one embodiment, the plaque composition for each stenosis comprises a plaque material established by (i) randomly selecting a center of each volume of plaque material; (ii) randomly selecting a size and a shape for the plaque material; (iii) randomly selecting material proprieties for the plaque composition; and (iv) establishing the plaque material using the center, size, shape, and material properties. In one embodiment, the plaque composition for each stenosis mimics a predefined high risk plaque composition.

In some embodiments, multiple machine learning models may be used with the aforementioned method. For example, in one embodiments, the machine learning models comprise a first machine model trained to predict plaque formation, a second machine model trained to predict plaque development, and a third machine model trained to predict plaque rupture. In other embodiments, the machine learning models include a first machine learning model trained to predict an ischemic weight of each branch, a second machine learning model trained to predict ischemic contribution scores, a third machine learning model trained to predict hemodynamic measures of interest, a fourth machine learning model trained to predict plaque related measures of interest, and a fifth machine learning model trained to predict a risk of future cardiovascular event. Where multiple machine learning models are employed, they may be applied in parallel to the features of interest in some embodiments. In some embodiments, the machine learning models are applied in a cascaded workflow that sequentially applies the machine learning models using outputs of each machine learning model as inputs for a subsequent machine learning model in the cascaded workflow.

Some embodiments of the aforementioned method further include visualization aspects. For example, in one embodiment, a visualization is generated depicting the measures of interest related to atherosclerotic plaque. In some embodiments, the visualization comprises a coronary artery image and, in response to user selection of a location within the coronary artery image, a measure of interest corresponding to the location is presented in the visualization.

According to another aspect of the present invention, a computer-implemented method for training a machine learning model to provide a personalized evaluation of assessment of atherosclerotic plaques for a patient includes generating a database of synthetic data comprising one or more of in silico anatomical models and performing FSG computations for the in silico anatomical models to yield output data. The method further includes extracting measures of interest from the output data, as well as geometric features of the in silico anatomical models and plaque-related features from the database of synthetic data. One or more machine learning models are trained to generate predicted measurements related to atherosclerotic plaque based on the geometric features of the in silico anatomical models trees and the plaque-related features.

According to other embodiments of the present invention, a computer-implemented method for predicting effects of a treatment plan includes extracting patient-specific geometry from medical images, as well as geometric features of interest and plaque related features of interest from the patient-specific geometry. One or more machine learning models are used to predict an effect of a treatment plan using the geometric features of interest and plaque related features of interest, wherein the machine learning models are trained using patient-specific features and longitudinal data related to effects of treatment plans. Additionally, in some embodiments, a report is generated in a structured format describing the effect of a treatment plan and the report may be stored in a patient-specific medical record.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawing. For the purpose of illustrating the invention, there are shown in the drawing exemplary embodiments that are presently preferred, it being understood, however, that the invention is not limited to the specific instrumentalities disclosed. Included in the drawings are the following Figures:

FIG. 4D presents a visualization of the third step of the method shown in FIG. 4A;

FIG. 4E presents a visualization of the fourth step of the method shown in FIG. 4A;

DETAILED DESCRIPTION

The following disclosure describes the present invention according to several embodiments directed at methods, systems, and apparatuses related to the personalized assessment of atherosclerotic plaque using machine learning (ML) techniques. More specifically, the techniques described herein use ML models to predict measures of interest related to plaque such as risk of a cardiovascular event, indication of a future screening date, plaque composition (absolute/relative values of plaque components), plaque evolution related measure of interest (future size, shape, composition and location of plaques), in-stent restenosis, lesions requiring sealing, therapy planning, etc. The prediction is based on various features extracted from non-invasive patient data, medical imaging data (e.g., noninvasive imaging (Computed Tomography (CT), Echocardiography (stress/rest, with/without contrast agent), Magnetic Resonance Imaging (MRI), etc.), invasive imaging (X-ray angiography, IVUS, OCT, NIRS)), blood biomarkers, radiogenomic information, wearable sensors, etc. One advantage of the ML based workflows discussed herein is that data from heterogeneous sources may be integrated to perform a comprehensive assessment.

Figure 1:
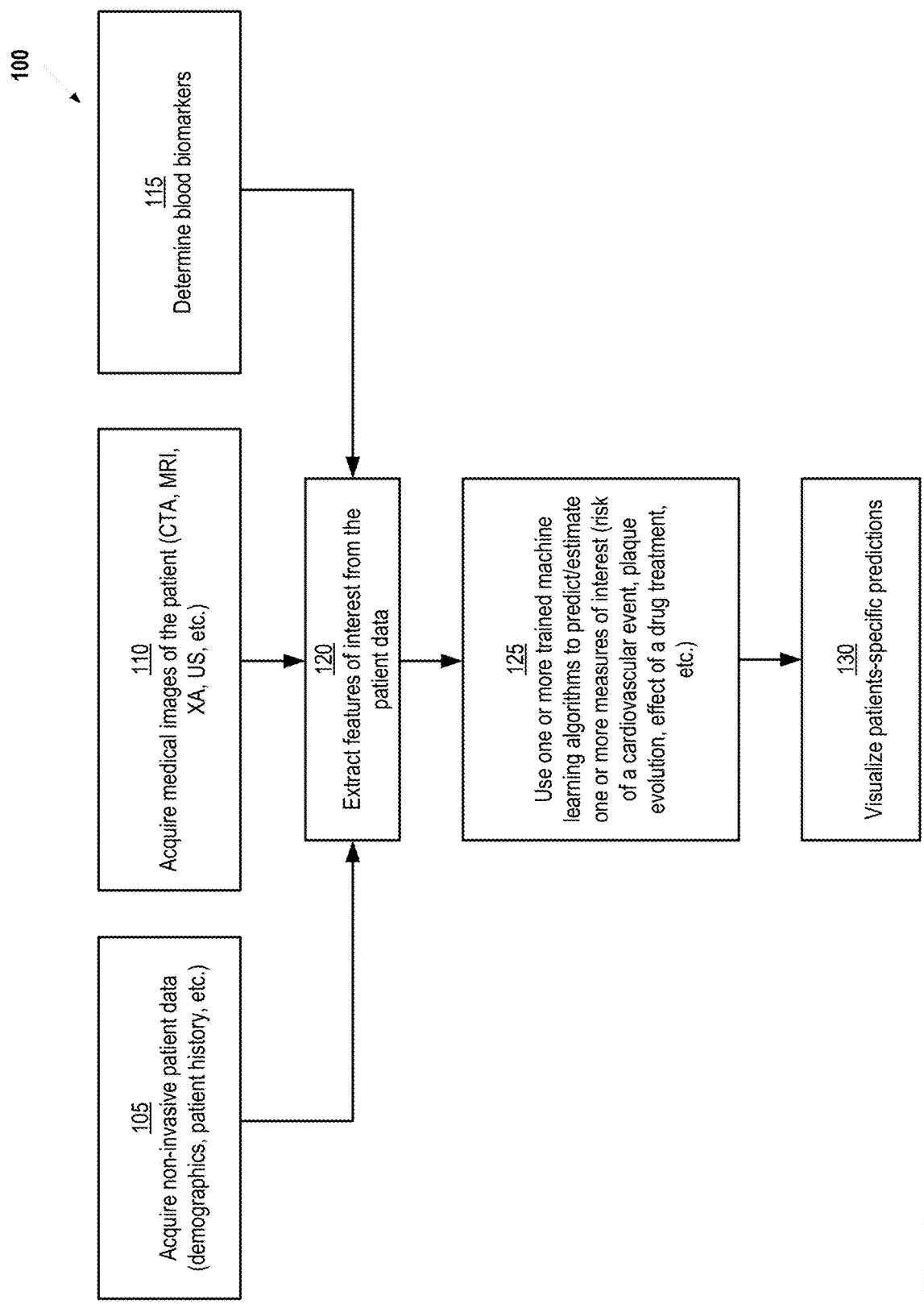
FIG. 1 shows a workflow used to predict measures of interest related to the formation, progression and rupture of plaque in the human cardiovascular system, according to some embodiments.

FIG. 1 illustrates a workflow 100 for predicting measures of interest related to the formation, progression, and rupture of plaque in the human cardiovascular system, according to some embodiments. Starting at step 105, non-invasive patient data is acquired. The term "non-invasive patient data" refers to any data that may be acquired using non-invasive techniques. Examples of non-invasive patient data that may be acquired at step 105 include, without limitation, demographics and patient history. The non-invasive patient data can be acquired via a wide range of sensors, comprising medical equipment and devices (stethoscope, blood pressure meter, imaging scanners, laboratory diagnostic, etc.) as well as non-medical grade devices (including, without limitation, wearables) for the measurements of physiological signals. In some embodiments, the non-invasive patient data includes biochemical signals as produced, for example, by blood tests and molecular measurements (e.g., "omics" such as proteomics, transcriptomics, genomics, metabolomics, lipidomics, and epigenomics). Additionally, the non-invasive patient data may span a wide range of biometrics signals, and can be driven by the individual as in the Quantified Self movement, promoting self-monitoring and self-sensing through wearable sensors and wearable computing. Furthermore, features extracted based on radio-genomics may be generated and used as non-invasive patient data (e.g., imaging biomarkers that are linked with the genomics of a pathology).

At step 110, medical images of the patient are acquired. Generally, any medical imaging technique known in the art may be used in acquiring the images at step 110. Thus, non-invasive imaging techniques may be applied at step 110 such as MRI, Computed Tomography (CT), Echocardiography (stress/rest, with/without contrast agent), as well as invasive imaging techniques such as X-ray angiography, Intravascular ultrasound (IVUS), Optical Coherence Tomography (OCT), and Near-infrared Spectroscopy (NIRS).

At step 115, blood biomarkers are determined based on blood measurements of the patient. These blood biomarkers may include, for example, Complement Reactive Protein, Fibrinogen, White Blood Cell Count, IL-6, IL-18 & TNF-α, Circulating Soluble CD40 Ligand, Vascular Calcification Markers (osteopontin, osteoprotegerin, etc.), Matrix Metalloproteinases, Myeloperoxidase, Platelet-derived growth factors, cardiac troponin I, cardiac troponin T, creatine kinase, creatine kinase myocardial band, total cholesterol, level of serum C-reactive protein, C-reactive protein, lactate dehydrogenase (LDH), aspartate transaminase (AST), myoglobin (Mb), ischemia-modified albumin (IMA), glycogen phosphorylase isoenzyme BB, High-density lipoprotein (HDL) cholesterol, low-density lipoprotein (LDL) cholesterol, pregnancy associated plasma protein A (PAPP-A), insulin-like growth factor binding protein-4 (IGFBP-4) and its fragments, myeloperoxidase (MPO), fatty acid binding protein (FABP), troponin C (TnC), D-dimer and high molecular weight fibrin degradation products, soluble CD40 ligand (sCD40L), cystatin C, human serum albumin (HSA), procalcitonin (PCT), glycogen phosphorylase isoenzyme BB (GPBB), serum amyloid A (SAA), retinolbinding protein 4 (RBP4), soluble lectin-like oxidized LDL receptor (sLOX-1), adiponectin (Adn), and the S100 protein.

The different types of information acquired at steps 105-115 may be obtained at a single time point or at different time points. For example, features extracted from a Cardiac Computed Tomography Angiography (CCTA) exam performed at a baseline state, and from an angiographic exam, performed at a later time point may be used to predict the measure of interest. Similarly, blood biomarkers (the same or different) may be acquired at different time points and used as features of the ML models, as described below.

Continuing with reference to FIG. 1, at step 120, features of interest are extracted from the non-invasive patient data, the medical images, and the blood biomarkers. Then, at step 125, one or more trained ML models are used to predict/estimate measures of interest such as risk of a cardiovascular event, plaque evolution, the effect of a drug treatment, etc. The ML models may be used in a cascaded or parallel workflow, and may be trained on patient-specific and/or on synthetic data, generated in vitro or in silico. For example, the training of the ML model(s) may employ physics based models to generate the output measures of interest against which the ML model is trained. Alternatively, the training may not require any physics based models, and may use only features extracted directly from the input data. Synthetic data may be further generated to enhance the database used during the training phase and the training may be performed on patient-specific data alone, synthetic data alone, or a combination of patient-specific data with synthetic data. ML models may furthermore be used to perform plaque histology/identification/segmentation. In one embodiment, deep learning based ML methods may be used with the ML models applied at step 125.

The measures of interest determined at step 125 can be defined at patient level or at lesion/plaque level. For example, in some embodiments the measures of interest determined at step 125 include the risk of a cardiovascular event related to atherosclerotic plaque (e.g., myocardial infarction related measures such as coronary circulation, stroke related measures such as cerebral circulation, and gangrene related measures such as peripheral circulation). The risk may be provided as a single score or as a time-dependent curve, it may refer to a specific period of time in the future, etc. In combination with the risk, an indication of a future screening date may also be provided (e.g., when to perform a follow up exam, so as to: confirm the prediction, perform an intervention if required, etc.). Additionally, plaque composition measures of interest may be predicted at step 125 such as absolute/relative values of plaque components (e.g., fibrous tissue, necrotic core, lipid pool, calcification, etc.), as well as plaque evolution-related measures of interest such as future size, shape, composition and location of plaques. Separate models may be used for the initiation, evolution, and rupture of plaque.

In some embodiments measures of interest related to in-stent restenosis may be determined at step 125. In-stent restenosis tends to appear 3-6 months after the stent placement, due to the proliferation of cells in the media layer (also called neointimal hyperplasia). Measures of interest may include, for example, degree of restenosis, time of onset, etc.

The measures of interest determined at step 125 may also identify lesions which require sealing. In combination with stents generated from bioresorbable scaffold, which have the ability to dissolve after restoring the patency of the vessel, sealing of underlying plaques prone to future growth, as predicted by ESS, may be used to improve long term evolution of coronary arterial disease (CAD) patients.

Therapy planning measures of interest may also be determined at step 125. In case a medical therapy is prescribed (e.g., following a baseline exam), the measure of interest may be related to the efficiency of the drug treatment (e.g., decrease of the risk for a cardiovascular event). In case of device therapies (such as stenting, grafting etc.), the measure of interest could be the viability/effectiveness of the device in the wake of plaque and/or thrombus initiation and growth.

Returning to FIG. 1, at step 130, the measure of interest determined at step 125 is presented to the clinician in a visualization. This visualization may be presented, for example, in a numeric (e.g., tabular) or in a graphical way (e.g., overlaid on the medical images).

Figure 2:
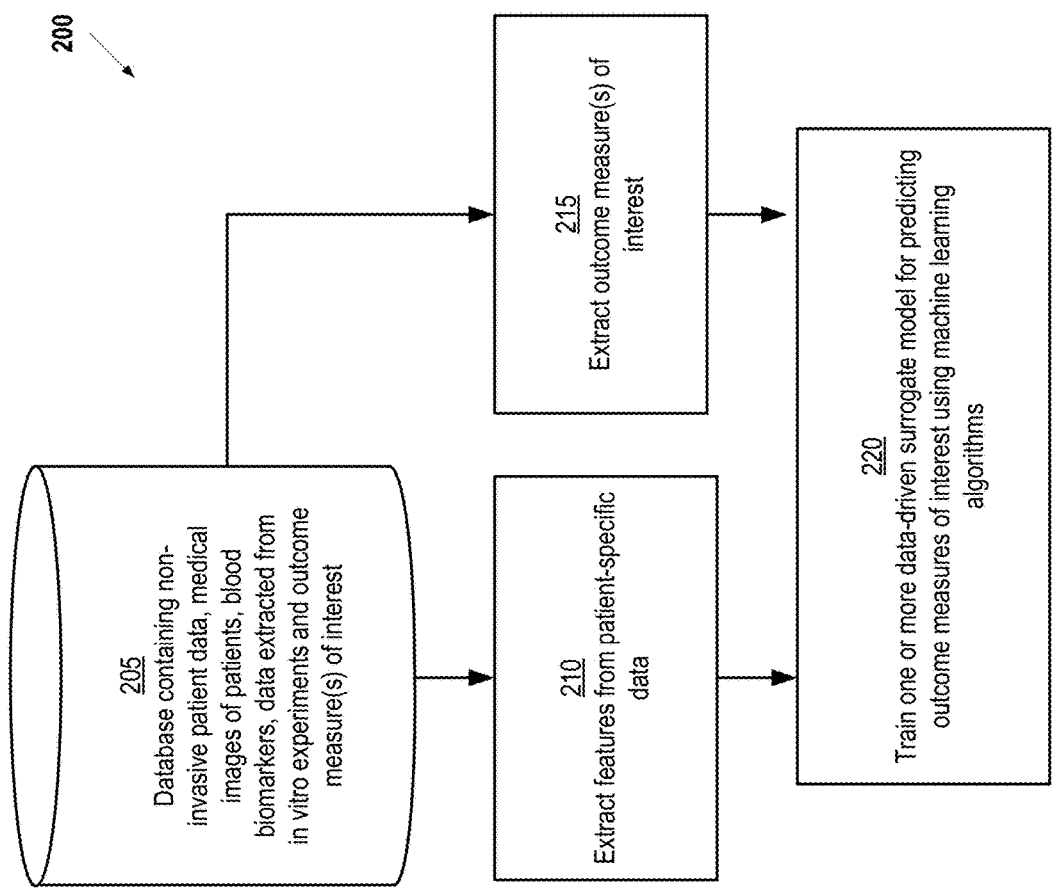
FIG. 2 shows a workflow used to train one or more data-driven surrogate models for predicting measures of interest related to the formation, progression and rupture of plaque in the human cardiovascular system, according to some embodiments.

The workflow displayed in FIG. 1 is used during the prediction phase which is performed online. To be able to use the ML models, the models may be trained a priori offline. FIG. 2 displays the generic workflow 200 of the training phase, as it may be performed in some embodiments. One of the requirements for the training phase in this example is the existence of a large database 205 containing synthetically generated and/or patient-specific information (non-invasive data, medical images, blood biomarkers), corresponding ground-truth, namely the outcome measures of interest for plaque evolution (e.g., risk of a cardiovascular event, plaque evolution). The database 205 may contain information from in vivo, in silico and in vitro studies. Once this database 205 is assembled, relevant features and the corresponding outcome measure(s) of interest are extracted at steps 210 and 215, respectively. Then, at step 220, the features and outcome measures of interest are used to train one or more data-driven surrogate models using ML models. During the training phase more features may be available than during the online prediction phase. The features which are missing during the prediction phase may be estimated based on similar datasets in the training database, (e.g., by employing a separate ML model specifically trained for this purpose). In one embodiment the training of the ML model(s) may employ physics based models to generate the output measures of interest against which the ML model is trained (as described in further detail below). In another embodiment, the training may not require any physics based models, and may use only features extracted directly from the input data.

One possible ML model which may be employed in workflows 100 and 200 shown in FIGS. 1 and 2, respectively, is deep tensor neural network (DTNN), which emerged from the tensor network theory applied in neuroscience (tensor interactions are encountered in the central nervous system). DTNN performs data regularization, ensuring thus that the underlying physics are captured, and leading to models which have generative power. Various variants of the DTNN may be used with the workflows 100, 200 including, without limitation, DTNNs that employ linear activations instead of sigmoidal nonlinearity may be used and directly connected to layers through a tensor, and DTNNs where the sigmoid nonlinearity is applied after the Kronecker product, instead of being applied directly to the double projection layers.

In some embodiments, the ML models utilized herein employ deep learning methods. The term "deep learning" generally refers to a category of artificial intelligence techniques, which are based on a plurality of information-processing layers. Hierarchical structures are employed, either for the learning features or representation or for classification/regression. Recently, deep learning based applications have improved on prior state-of-the-art results in several areas of research, like voice recognition (natural language processing), computer vision, optical character recognition, signal processing, information retrieval, etc. The deep learning techniques may be categorized into synthesis/generation or recognition/classification. Thus, three main deep learning classes may be considered. Within the first class, discriminative models are developed for delivering high discriminative power either in classification or regression applications. In the second class, generative models are developed for characterizing the higher-order correlation characteristics of the available data for synthesis/analysis. These models may be employed to characterize the mutual statistical properties of the data and the corresponding classes. If, additionally, a Bayes rules is used, a discriminative version of the model is generated. Finally, in the third class, hybrid models may be utilized to perform both discrimination (classification/regression) and characterization of the samples.

One example of a generative model is a deep autoencoder which is a special type of deep neural network that outputs a transformed version of the input data. It is used for learning either dimensionality reduction or efficient encoding. It extracts non-linear features without making use of class labels. Thus, an autoencoder is generative and employs at least three layers: an input layer comprising input data; an output layer that same size as the input layer, whereas each unit corresponds to exactly one unit in the input layer; and one or more hidden layers (typically with fewer units than the input and output layers) that generate the encoding.

Figure 3:
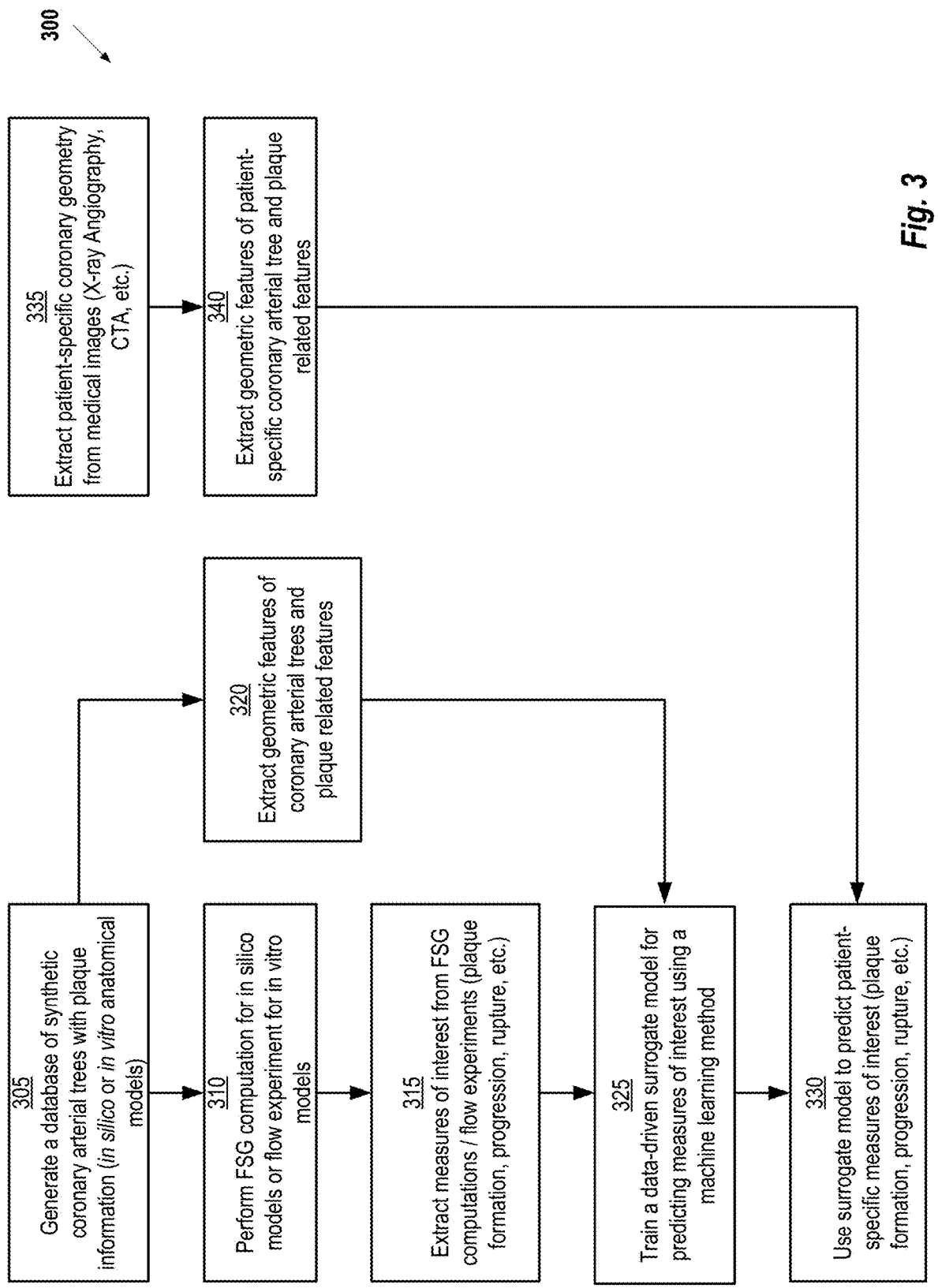
FIG. 3 shows a workflow for computing patient-specific plaque related measures of interest, according to some embodiments.

To further illustrate the techniques described herein, consider an embodiment wherein an ML model is trained based on a synthetic data to predict patient-specific plaque related measures of interest (e.g., plaque formation, progression, rupture, etc.). Here, synthetic data refers to data that is not specific to a particular individual, but rather data generated by using an algorithm, model, or a physical experiment. FIG. 3 illustrates a workflow 300 for computing patient-specific plaque related measures of interest for this example. Starting at step 305, a database is generated with synthetic coronary arterial trees. These trees may be generated using either in silico or in vitro techniques. Next, at step 310, fluid solid growth (FSG) computations are performed for the in silico anatomical models or flow experiments for the in vitro anatomical models. Various types of plaque growth models (described above) may be applied ranging from very simple to very complex models. These plaque growth models can be coupled with the fluid-solid interaction model. Based on these computations/experiments, one or more plaque related measures of interest are extracted at step 315. In parallel with steps 310-315, geometric and/or morphological features are extracted from the anatomical model at step 320. Then, at step 325, data-driven surrogate model(s) are trained using the geometric features and the target measure(s).

Continuing with reference to FIG. 3, once the surrogate model has been trained, it is applied at step 330 to predict patient-specific geometries obtained from medical images (X-ray angiography, CTA, etc.). For example, at step 335 in FIG. 3, patient-specific coronary geometries are extracted from medical images. The geometric features of the patient-specific coronary arterial tree and plaque-related features are next determined at step 340. These features may then be used as input data for the surrogate model. The missing features can be either predicted from a separate ML model, or estimated using similar anatomies in the database of synthetic geometries. FIG. 3 refers specifically to the coronary circulation, but the methodology may be applied similarly for other parts of the cardiovascular system.

Figure 4A:
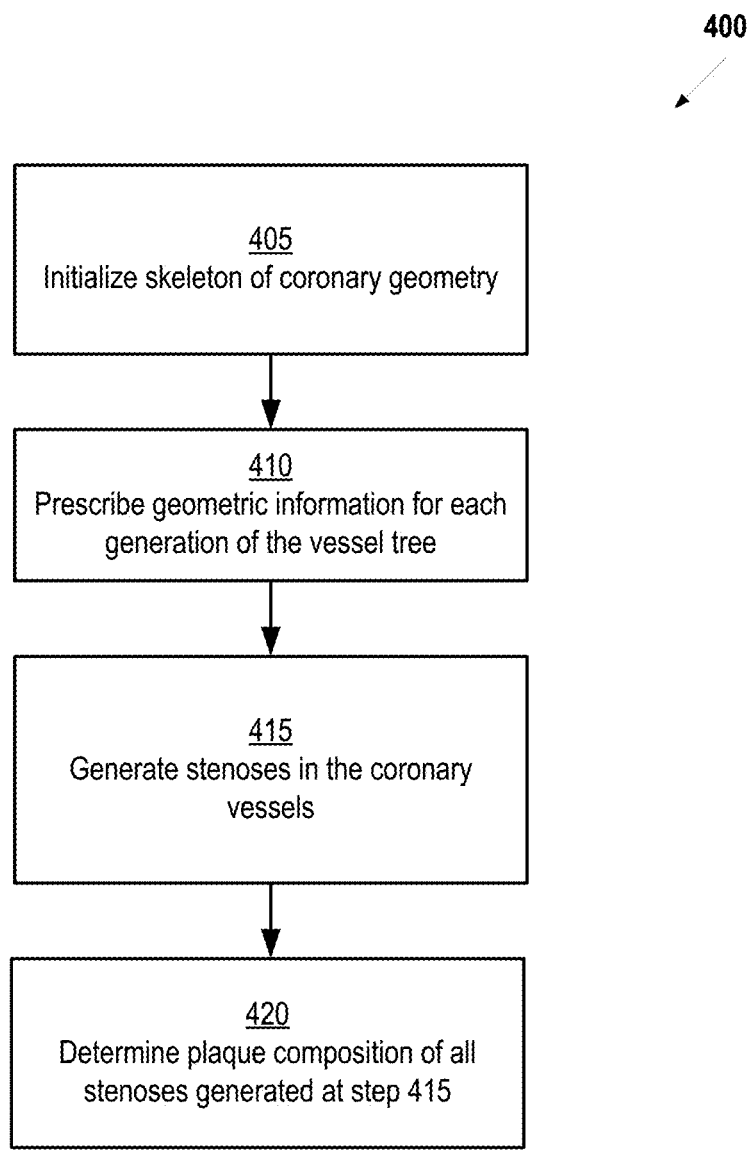
FIG. 4A presents a visualization of a method for generating synthetic in silico pathologic coronary geometries, according to some embodiments.
Figure 4B:
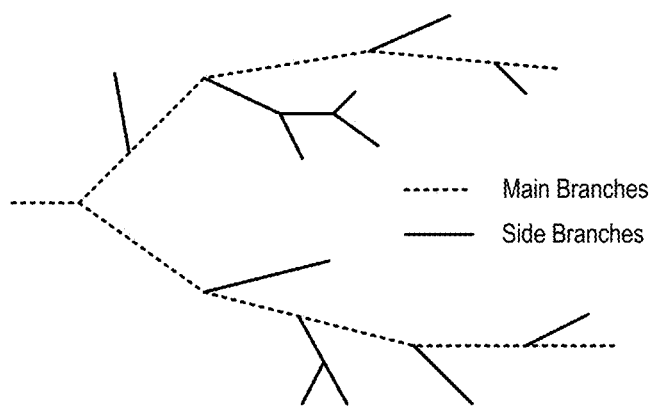
FIG. 4B presents a visualization of the first step of the method shown in FIG. 4A.
Figure 4C:
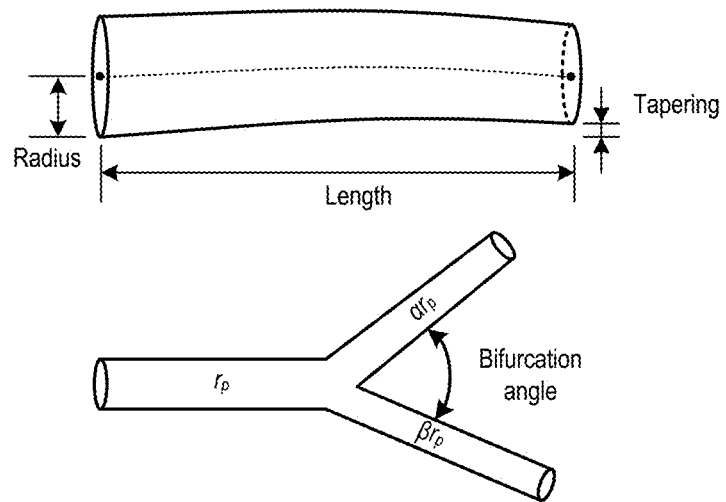
FIG. 4C presents a visualization of the second step of the method shown in FIG. 4A.

FIG. 4A illustrates a method 400 for generating synthetic in silico data, according to some embodiments. Starting at step 405, the skeleton of the coronary geometry is initialized, by prescribing the number of vessels at each generation of the tree (as visualized in FIG. 4B). At step 410, geometric information such as vessel radius, degree of tapering, branch length is prescribed for each generation of the vessel tree (as visualized in FIG. 4C). At step 415, stenoses are generated in the coronary vessel trees (as visualized in FIG. 4D). Then, at step 420, the plaque composition for all stenoses generated at step 415 is determined (as visualized in FIG. 4E).

Aside from the plaque composition determined at step 420 of the method 400, in some embodiments, other plaques may be generated which do not cause a constriction (e.g., plaques which lead only to positive remodeling). Various approaches can be followed to determine the type/composition of these synthetically generated plaques. For example, in some embodiments, the type of the synthetically generated plaques is randomly selected from a predefined list of plaque types (e.g., thin-cap fibroatheroma, predominantly fibrous plaque, etc.). Random selection may also be used to select the center of each volume of plaque material (e.g., center of necrotic core, center of lipid core, etc.), as well as the shape and size of each volume of plaque material and its material properties. Additionally, the synthetically generated plaques may be generated so as to mimic a geometric appearance that is typically associated with "high risk plaque", such as a napkin-ring shape and spotty calcification, a thin cap, etc. An important aspect is also the determination of the material properties of the arterial wall; these are prescribed during step 410.

Some of the flow related features that may be used by the ML models have been previously described in U.S. Pat. No. 9,349,178 to Itu et al., issued May 24, 2016, entitled "Synthetic data-driven hemodynamic determination in medical imaging," the entirety of which is incorporated herein by reference. Additionally, plaque related features may be extracted including, without limitation, the size/shape/volume of the plaque, the location of the plaque, the degree of positive remodeling, and the plaque composition (e.g., volume/percentage for each type plaque component). Furthermore, more advanced features can be defined, similar to the ischemic weight and ischemic contribution score. These advanced features may include, without limitation, plaque formation score (e.g., features describing the likelihood of plaque development at a certain location) and plaque growth score (e.g., features describing the growth speed of the plaque. Different growth factors can be defined for the different components of the plaque. Additionally, advanced features may be defined based on plaque rupture score (e.g., features describing the likelihood of a rupture of the plaque and plaque thrombus score (e.g., features describing the likelihood of thrombus formation of the plaque surface). The aforementioned advanced features may be derived from the basic features (e.g., geometry, plaque morphology, etc.) using mathematical operators, or may be determined by separate ML models.

The above described methodology refers to a workflow where the synthetic coronary geometries are generated directly with plaque information. Alternatively, healthy coronary geometries could be generated (with no plaque), and the ML model could predict the locations of plaque formation. The feature set could, in this case, be augmented with other synthetically generated features that are extracted from the patient data during the online application of the learned model. These features could be related to blood biomarkers (e.g., cholesterol), characteristics like arterial systemic pressure, or demographics.

Figure 5:
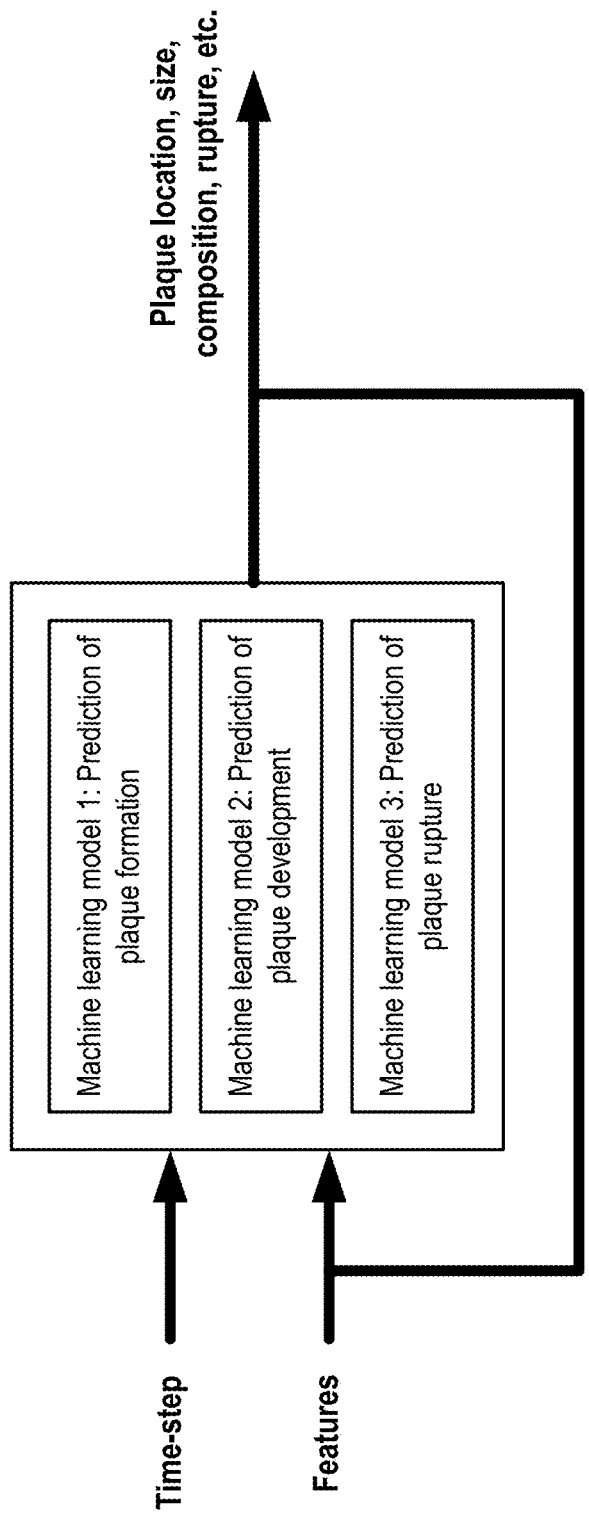
FIG. 5 illustrates a parallel machine learning based prediction of plaque formation, development and rupture, according to some embodiments.

In some embodiments, multiple types of ML models could be trained based on different FSG model versions. As illustrated in FIG. 5, these models can then be used in parallel for the prediction of plaque formation, development, and rupture. Each model uses as input a set of features (as described above), and also a time-step, to determine the various plaque related measures of interest for a certain future moment in time. This parallel model approach can then be applied iteratively to determine the evolution in time of the plaques/patient. Additionally, a confidence metric could be associated with the outputs. For example, this confidence metric can be defined such that the smaller the time step/the shorter the time-span predicted by the ML model, the higher the confidence will be.

Figure 6:
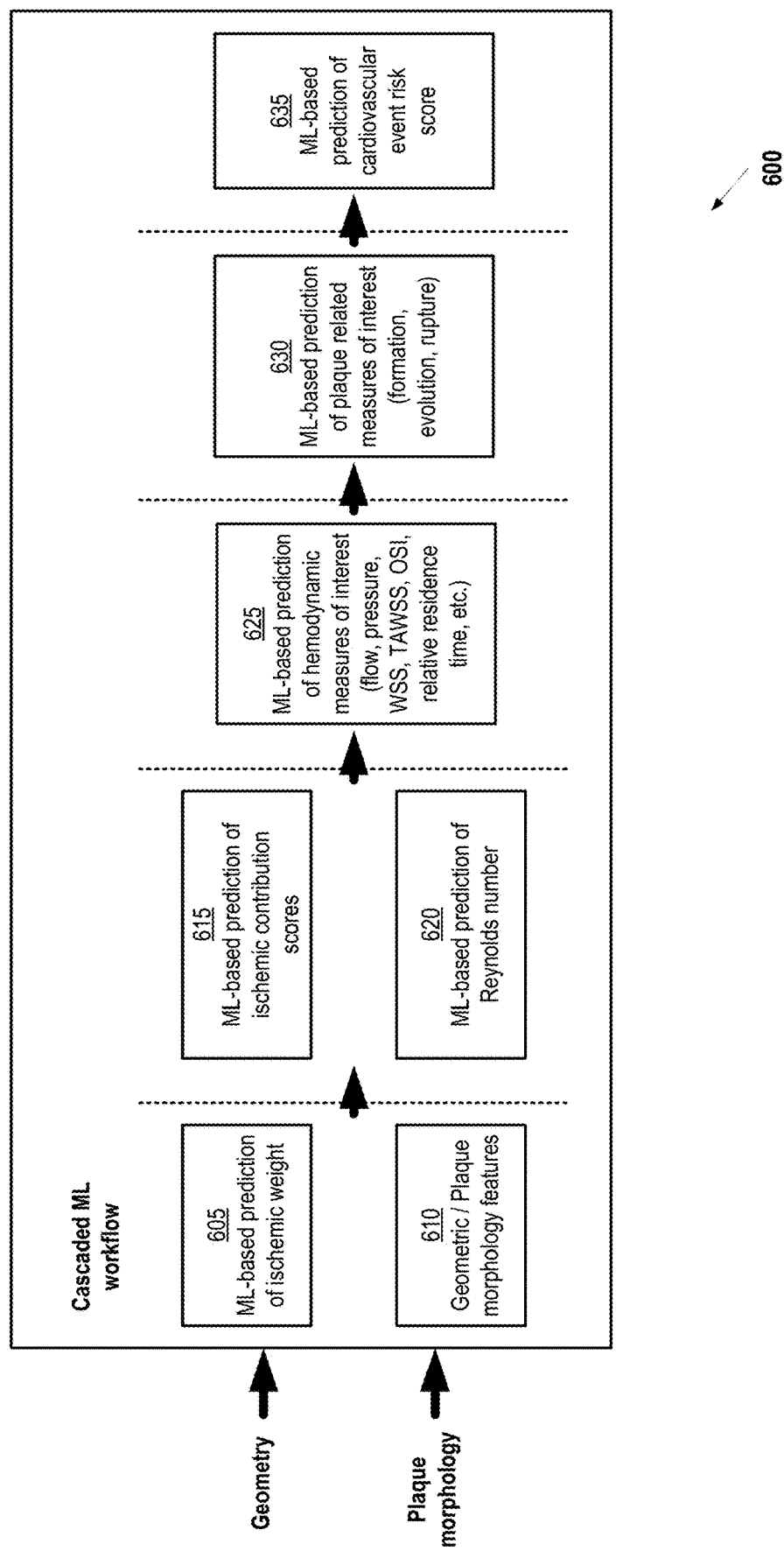
FIG. 6 shows a cascaded machine learning based workflow for the prediction of plaque related measures of interest, according to some embodiments.

FIG. 6 illustrates a cascaded ML-based workflow 600 for the prediction of plaque related measures of interest, according to some embodiments. As mentioned above, the more advanced features could be themselves generated with ML models, leading to a multi-level cascaded approach. The example of FIG. 6 uses as input only geometrical features of the vessel anatomy and of the plaque morphology. Each level in this cascaded workflow uses as features the outputs of the preceding ML levels. At the first level, the ischemic weight of each branch is computed at step 605 and the geometric/plaque morphology features are determined at step 610. At the second ML level, the ischemic contribution scores are computed at step 615 and the Reynolds number at each location of the arterial structure is determined at step 620. Next, at the third ML level hemodynamic measures of interest (e.g., flow, pressure, WSS, TAWSS, WSSG, OSI, relative residence time, presence of helical flow, tissue stress, etc.) are predicted at step 625. During the fourth ML level, the plaque related measures of interest are computed. Finally, at the fifth ML level the risk of future cardiovascular event is predicted at step 630.

The ML models described above use completely synthetic data during the training phase. The result predicted by the ML model for patient-specific data can potentially be improved by using patient characteristics. Hence, in the above described cascaded ML workflow, an additional level may be introduced. First a result is predicted by the algorithm which was taught on purely synthetic data and, then, the final ML algorithm uses the result predicted by the previous algorithms as features, alongside patient characteristics, in order to improve the final prediction.

The features for the second ML algorithm may include, for example, patient demographics, pathological history, previous cardiovascular history, non-invasive stress test results, exercise electrocardiogram (ECG) stress test results, exercise radioscope test results, blood biomarkers, and medications used in the past or present by the patient. One possibility is to build a database with the patient-specific data of previous cases and to use this database during the cascaded ML approach. As described before, during the first step, the ML algorithms taught on synthetic data are used to generate a first prediction of the measure of interest. During the second step, the features extracted for the patient specific data are used to find similar cases in the patient database and a final ML model is applied for predicting the final value of the measure of interest.

Figure 7:
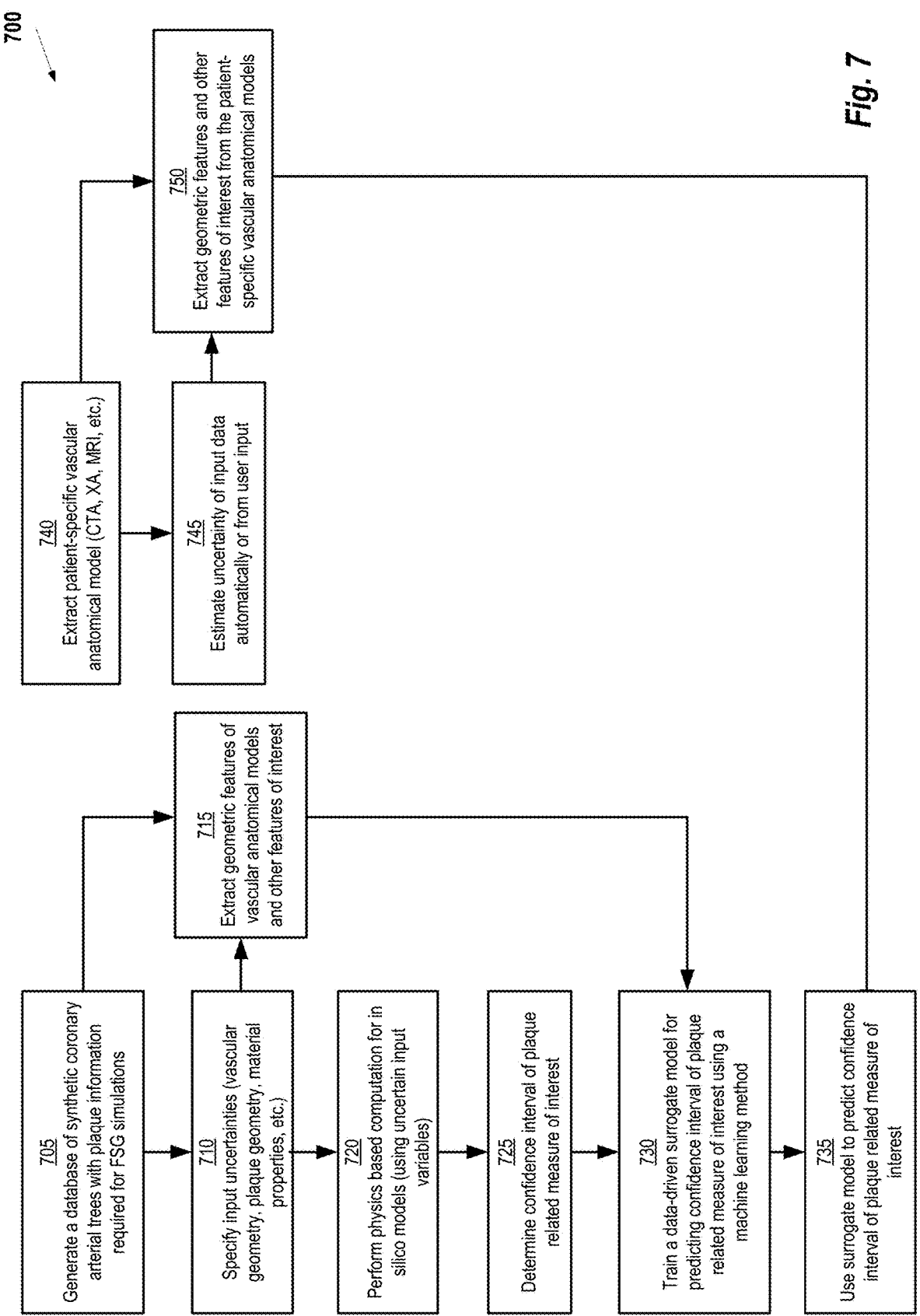
FIG. 7 illustrates an example workflow for estimating the uncertainty of plaque related measures of interest metric using a machine learning (ML) model, according to some embodiments.

In some embodiments, separate ML models may be used to provide a confidence interval for the estimation of a plaque related measure of interest, as shown in the workflow 700 presented in FIG. 7. Briefly, the first step is to use a set of uncertain input variables in the synthetic data (e.g. vessel diameter, plaque volume, etc.), propagate this uncertainty through the FSG model and determine the uncertainty for the measure of interest. The uncertainty can then be learned through an ML model based on the extracted features. The same features are then extracted for a patient-specific geometry and uncertainty in the input data is specified either automatically or by the user, and, using the ML model, the confidence of the estimated measure of interest metric is provided. Because such a ML model requires a large database, FIG. 7 is described below with reference to a database composed of synthetic data; however, it should be understood that a database comprising synthetic and/or patient-specific data may likewise be used. Additionally, FIG. 7 refers specifically to the coronary circulation, but the methodology detailed in this example may be applied similarly for other parts of the cardiovascular system.

Starting at step 705 in FIG. 7, a database is generated comprising synthetic coronary trees with plaque information, as required for FSG simulations. Next, at step 710, input uncertainties are specified, for example, by the user or based on previously used settings. These input uncertainties may pertain to, for example, the vascular geometry, the plaque geometry, material properties, etc. Based on the information collected at steps 705 and 710, at step 715, the geometric features of vascular anatomical models and other features of interest are extracted. Next, at step 720 physics-based computations are performed for in silico models using the uncertain input variables specified at step 710. Then, based on the results generated from step 720, a confidence interval is determined at step 725 for each plaque-related measure of interest.

Continuing with reference to FIG. 7, at step 730, a data-driven surrogate model is trained to predict a confidence interval of plaque related measures of interest using an ML-based method. At steps 740-745 a patient-specific vascular anatomical model is extracted from imaging data (CTA, XA, MRI, etc.) and the uncertainty of the data is estimated automatically or from user input. Additionally, at step 750, geometric features and other features of interest are extracted from the patient-specific vascular anatomical models. Finally, at step 735, the surrogate model is used to predict a confidence interval of the plaque-related measure of interest using the data generated at step 740-750.

As described above, one possible application of the techniques described herein is to determine a future screening date for the patient. Thus, when the patient undergoes this screening exam, a new dataset, besides the baseline data becomes available. In general, if multiple datasets are available for a patient, this additional information can be used to further improve the ML based predictions. For example, the features extracted from the additional information may be used directly as input features. Also, the features extracted from the additional information may be used at an intermediate level of a cascaded ML approach (e.g., for the workflow in FIG. 6). These additional features may be used as input data at the fourth level to obtain a better prediction of plaque formation, evolution and rupture. Furthermore, subsequent exams may be scheduled not only for screening purposes, but also in case of minor/major cardiovascular events.

In some embodiments, the techniques described herein are capable of including information extracted from measurements: if the measurement of a plaque related feature is available (e.g., as acquired through IVUS or OCT), the system can use this information to improve the accuracy of the prediction everywhere. Further, the error in the original prediction at the location where data is provided can be used to improve the model's future performance. The users' corrective actions taken to improve automatically identified features can be used to improve the feature detection in the future. The system may be able to learn from the user inputs. Further, if additional data on the outcomes becomes available, the learned model can itself be continuously improved. This improvement can be performed at global level or in a site-specific manner. This allows the system to account for anatomical trends based on patient demographics. If measurements of plaque related features become available, the system can automatically or semi-automatically identify outlier cases. These cases can then be used to create a new set of synthetic geometries which mimic the features of the outlier, together with the already available training set to improve the model predictions. In addition to anatomy, if plaque related measurements are also available (e.g., via IVUS or OCT), then they can also be incorporated in the machine learning approach. To do this, the training data is appended with new features characterizing plaques. In the prediction phase, if the measured values of these 'plaque' related features are available, they could be used as features. In their absence, the model can be used to find similar patients from the database from the geometric features to arrive at data-driven estimates of plaque features in different branches.

Figure 8:
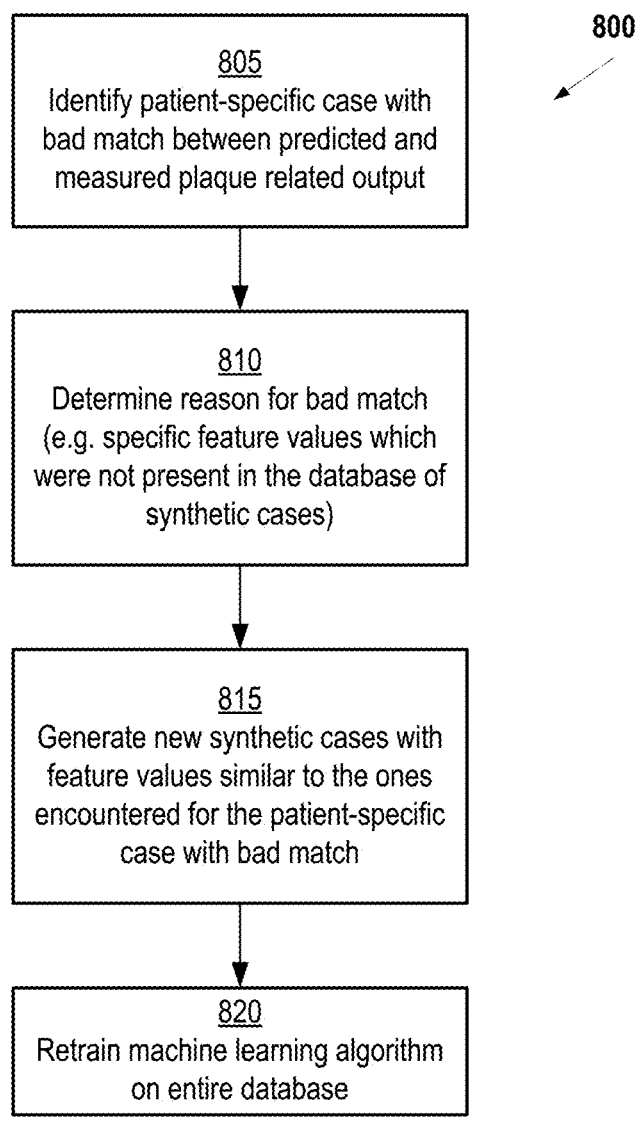
FIG. 8 presents a technique to retraining an ML model based on patient-specific cases with bad match between predicted and measured plaque related metric of interest, according to some embodiments.

Although a very large number of synthetic cases can be generated for training the ML algorithm, these will typically not cover all patient-specific cases. Hence, when using the ML algorithm to predict results for patient-specific data, bad matches between predicted and measured output might appear. In this case, the workflow 800 displayed in FIG. 8 can be used to enrich the database of synthetic cases so as to improve the prediction for the patient-specific cases which lead to a bad match. The workflow 800 may also be performed directly on the workstation (since the generation of synthetic data can be fully automated). Starting at step 805, a patient-specific case that is a bad match between the predicted measurements and the acquired patient-specific measurements is identified, for example, manually by the user or automatically with an ML-approach based on the presence of one or more features in the data. The term "match" here is somewhat flexible in that the tolerance for determining when two measurements are equivalent can be adjusted as desired. For example, in some embodiments, the acceptable range of values for the predicted measurements may be limited to values within 1% of the measured values. In other embodiments smaller or larger percentages may be used depending, for example, on the type of data being measured. Continuing with the workflow 800, at step 810, the reason for the bad match is determined, again either based on user input or using an ML model. At step 815, new synthetic cases are generated with feature values similar to the ones encountered in the case with the bad match. Then, at step 820, the ML model is retrained on the entire database.

Figure 9:
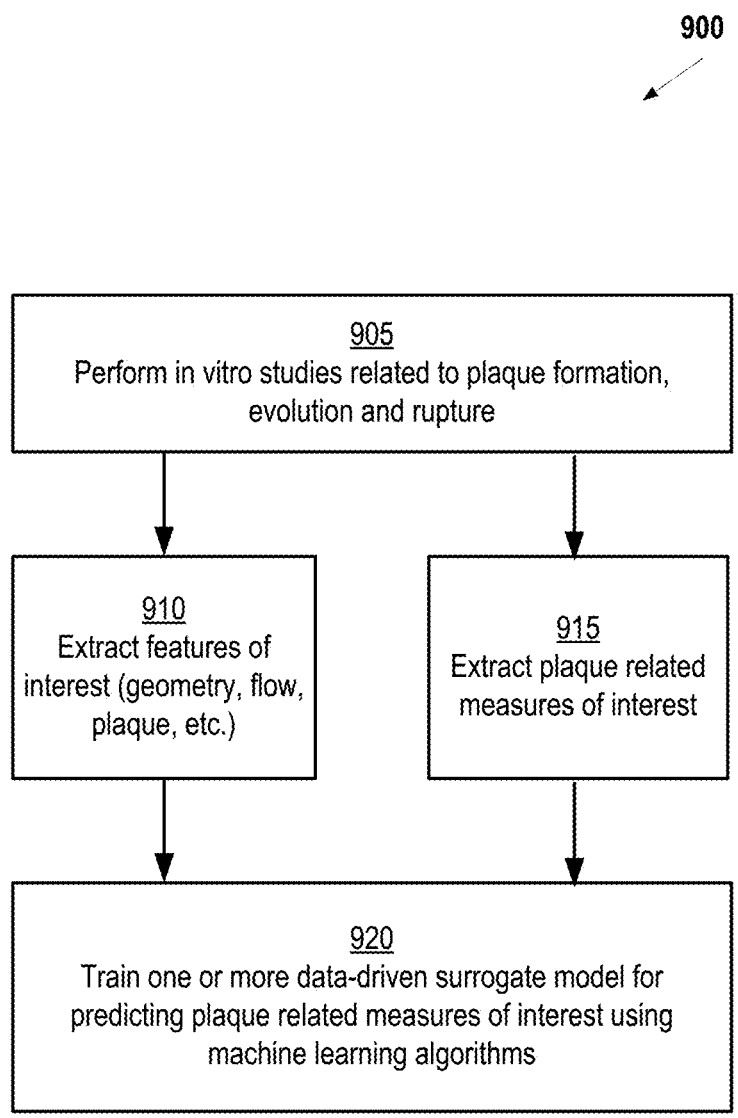
FIG. 9 illustrates a workflow for training an ML model on in vitro data for predicting plaque related measures of interest, according to some embodiments.

In vitro studies are an important alternative for studying plaque formation, evolution and rupture. Since the experimental conditions can be controlled exactly in in vitro studies, an ML model can be trained to predict the formation, evolution and rupture of plaques using a database built from such studies as shown in the workflow 900 presented in FIG. 9. At step 905, in vitro studies are performed related to plaque formation, evolution, and rupture. Next, at steps 910 and 915 features of interest and plaque-related measures of interest are extracted. The features of interest may include, without limitation, the geometry of the artificial vessel, the hemodynamics in the artificial vessel (e.g., flow rate, velocity, pressure, shear stress, etc.) obtained through direct or indirect measurements, and plaque composition. Then, at step 920, one or more data-drive surrogate models are trained for predicting plaque-related measures of interest using ML models.

Figure 10:
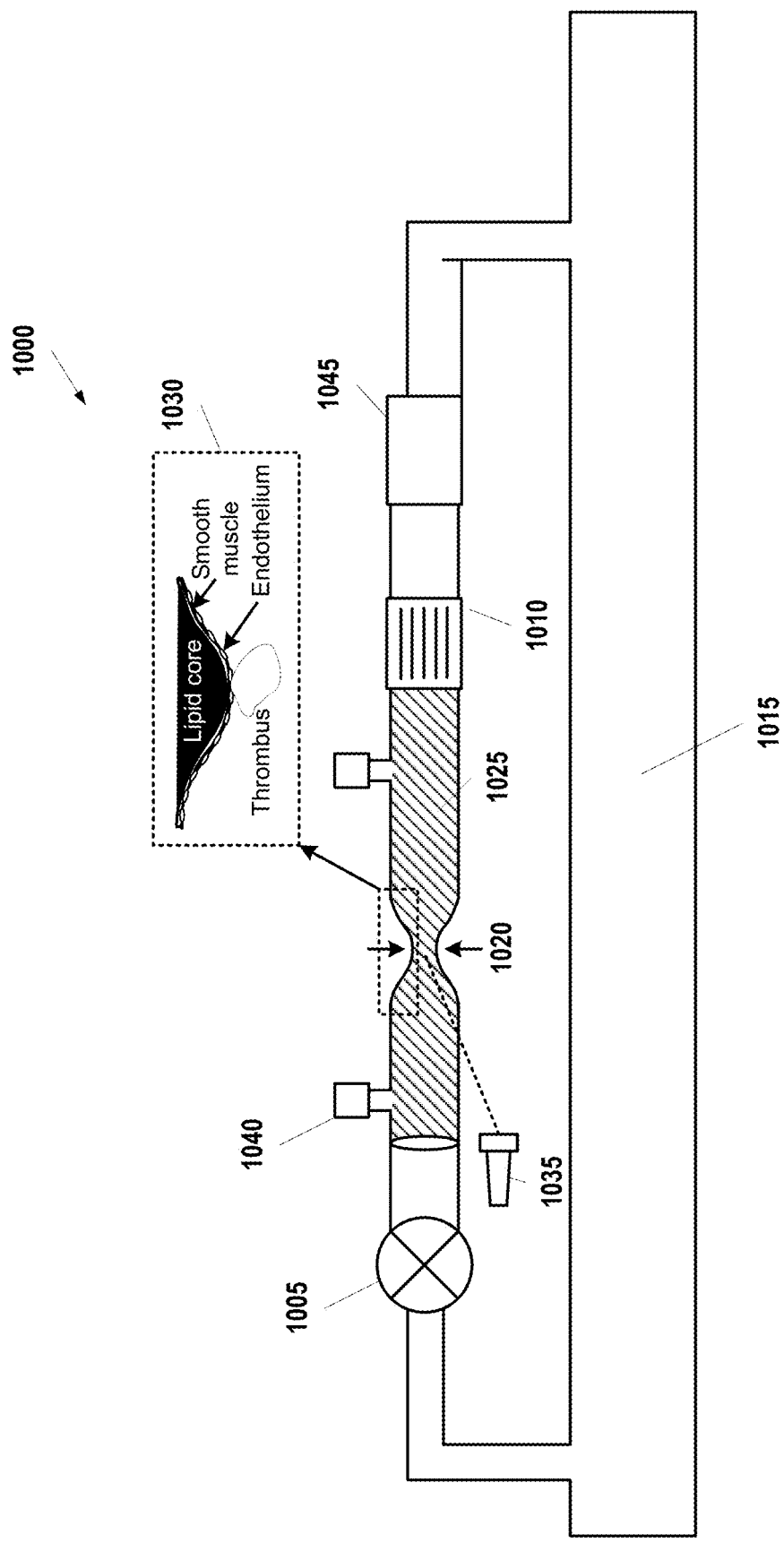
FIG. 10 shows an example in vitro model used for generating the training database in some embodiments.

FIG. 10 illustrates an example in vitro model 1000 that may be used for generating the training database, according to some embodiments. The model 1000 includes an Artificial In Vitro Vessel 1025 (or vessel tree). A Pump 1005 circulates a fluid with properties similar to the ones of human blood through the in vitro model. Hydraulic Resistances 1010 are coupled to the terminal in vitro segments. Together with the Pump 1005, the Hydraulic Resistances 1010 generate realistic levels of pressure inside the in vitro model 1000. A Reservoir 1015 collects the fluid. One or more Occluders 1020 generate constrictions in the in vitro model 1000.

Cardiovascular Tissue 1030 (endothelium, plaque material, etc.) is placed on the inside surface of the Artificial In Vitro Vessel 1025. For example, basic human in vitro models of atherosclerosis may comprise simple endothelial cultures treated with certain risk factors (inflammatory factors, oxidized low density lipoprotein, high levels of glucose) and co-cultures which include human leukocytes or smooth muscle cells. The model 1000 may also include various measurement devices for determining the hemodynamic measures including Pressure Transducers 1040, Flow Meters 1045, and a Doppler Probe 1035 for measuring the fluid velocity. Additionally, a pressure or flow measurement catheter (not shown in FIG. 1000) may be used to add the influence in high degree stenosis or small diameter vessels on the measured quantity.

The in vitro model 1000 may be modified in numerous ways to generate a large number of setups. For example, the following characteristics may be varied in different embodiments: the number, position and shape of the occluders; resistances; pump action; number of side branches (total occlusion may be induced); heart movement, breathing (4d in-vitro model); heart rates, flow, flow curves, any specific coronary or heart disease, bypass, effect of collateral flow; plaque type (e.g., TCFA, eroded plaque, etc.); plaque composition; fluid composition (e.g., cholesterol level). Furthermore, the above described in vitro studies may be performed at normal or microfluidic scale, and in 2D or in 3D.

In vitro studies, similar to the one displayed in FIG. 10, may be alternatively used to derive a simplified version of a mathematical representation of plaque formation, evolution and rupture (simplified version of plaque related governing equations). Although great advances have been reported in developing ML-based models for real-time prediction of dynamic processes, these models can only be applied under conditions which were considered during the training of the ML model. Hence, these models cannot extrapolate beyond the range of feature values considered during the training phase.

To extrapolate beyond the range of feature values considered during the training phase, in some embodiments an approach based on the theory of dynamical system discovery is utilized. The main idea is that the majority of physical processes can be modeled with only a few terms that are most relevant for the dynamics of the system. Thus, the governing equations can be considered to be sparse in a high-dimensional nonlinear function space, and represented as:

$$\frac{d}{dt}x(t) = f(x(t)),$$

where x is the state vector and f represents the dynamic constraints of the system. Note that, with this approach, the time history of the state vector is collected and used. Model complexity and accuracy are naturally balanced. The derivative of the state vector is either measured or determined numerically from the time history of the state vector.

An important step of the identification problem is the specification of the candidate nonlinear functions (there is no limitation in the choice of functions). If basic knowledge of the physics behind a given identification problem is available, it may be used to derive candidate nonlinear functions. For example, in case of plaque related applications, various growth models have been proposed in the past. Various approaches may be then used to determine which nonlinear terms are active for a given identification problem.

Figure 11:
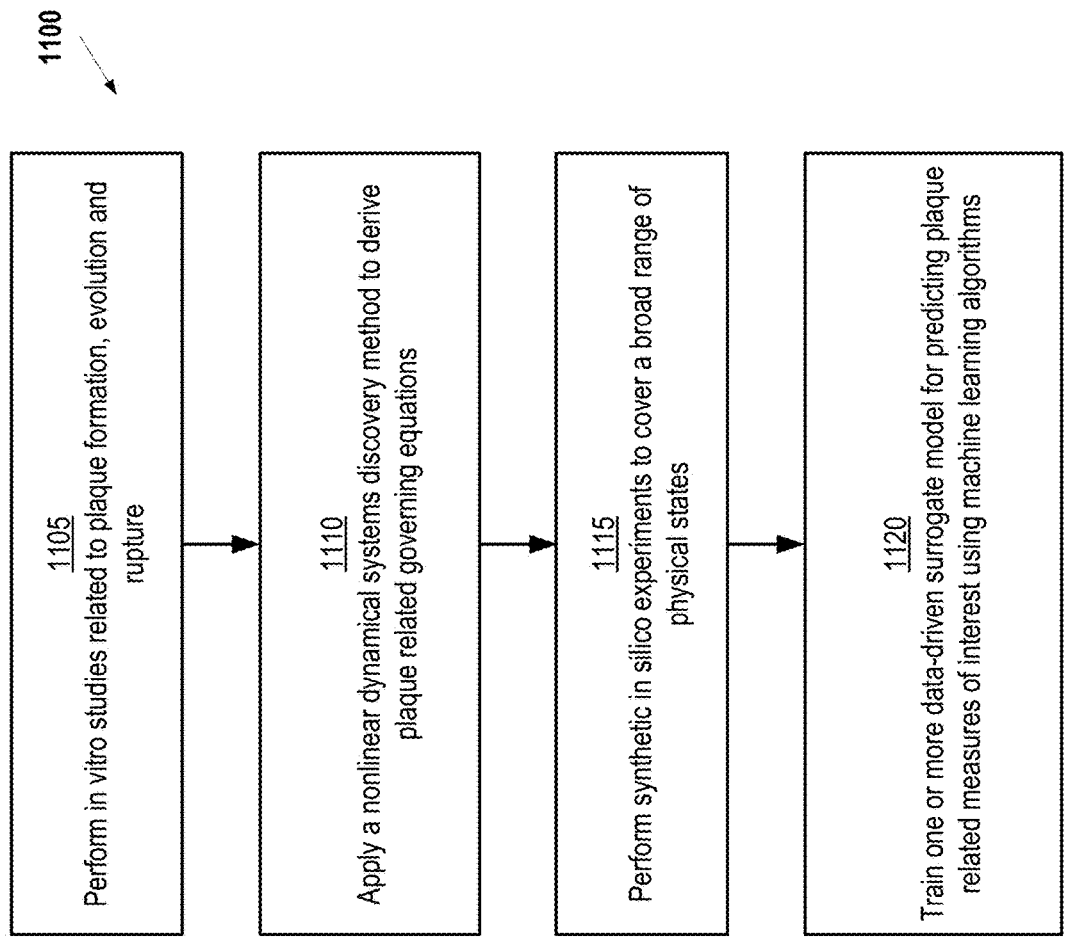
FIG. 11 shows a workflow for training an ML model on in silico data generated from a physics based model derived from in vitro data, according to some embodiments.

FIG. 11 shows a workflow 1100 for training an ML model on in silico data generated from a physics based model derived from in vitro data, according to some embodiments. This workflow 1100 is an extension of the workflow in FIG. 9, which is based on the above described methodology for dynamical system discovery. Starting at step 1105, in vitro studies are performed which span a large but finite variety of conditions (in terms of geometry, hemodynamics, plaque composition and structure, etc.). At step 1110, the nonlinear dynamical systems method is applied to derive simplified governing equations related to plaque formation, evolution and rupture. Next, at step 1115 a methodology similar to the one described above with respect to FIG. 4 is used for generating synthetic in silico data, herein based on the models derived at step 1110. Then, at step 1120, one or more ML models are trained for predicting in real-time plaque related measures of interest based on the synthetic data generated at step 1115.

This workflow 1100 shown in FIG. 11 combines the advantages of the methods and workflows described in the previous sections, because it incorporates information extracted from in vitro models simulating realistic plaque related hemodynamics. Because simplified governing equations are learned based on these experiments, one can extrapolate beyond the conditions encountered in the in vitro studies (due to objective constraints like time and budget, typically only a limited amount of in vitro studies can be performed). However, depending on the nature of the derived governing equations, these may allow only for numerical solutions, which in turn require large execution times. By running synthetic in silico experiments based on the governing equations, and learning the mapping between a given set of input conditions and the plaque related measures of interest, real-time based prediction can be achieved.

An alternative to the nonlinear dynamical systems discovery method has been recently introduced and termed field inversion and machine learning (FIML). This technique has been used for complementing existing mathematical models so as to obtain a better match with experiments. Inverse modeling techniques are employed to derive corrective terms (which may be spatially and/or temporally distributed), and ML techniques are used to reconstruct the model corrections (i.e., additional functional forms that appear in the model).

Figure 12:
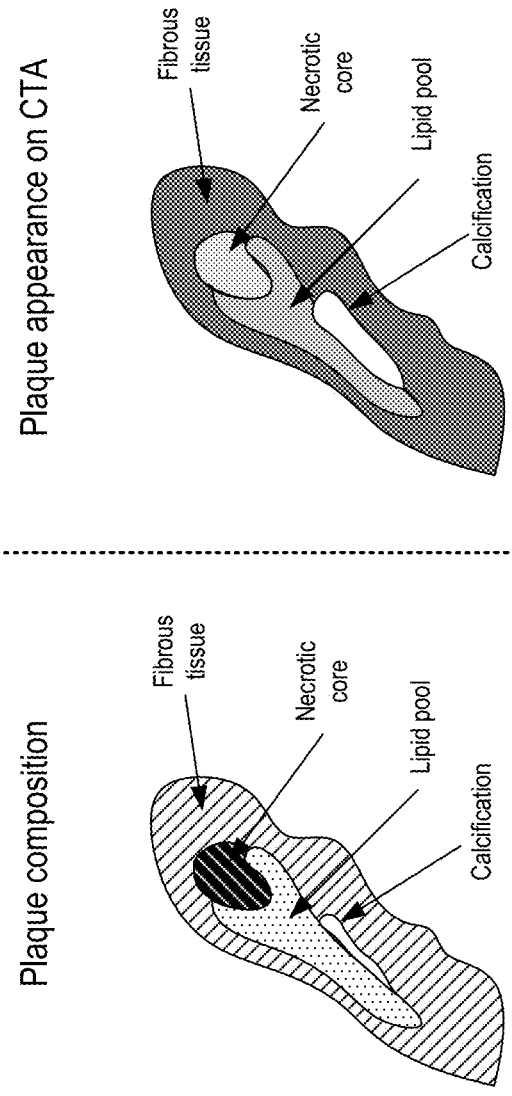
FIG. 12 illustrates an atherosclerotic plaque with main constituents and plaque appearance on a Computed Tomography Angiography (CTA) image.

ML models may also be used to perform plaque histology on medical images. For example, FIG. 12 shows on the left an atherosclerotic plaque with four main components and on the right side its appearance on a CTA image: different plaque constituents have different densities and thus lead to a different appearance on medical images (e.g. lipid density was found to be lower than collagen or smooth-muscle density).

Figure 13:
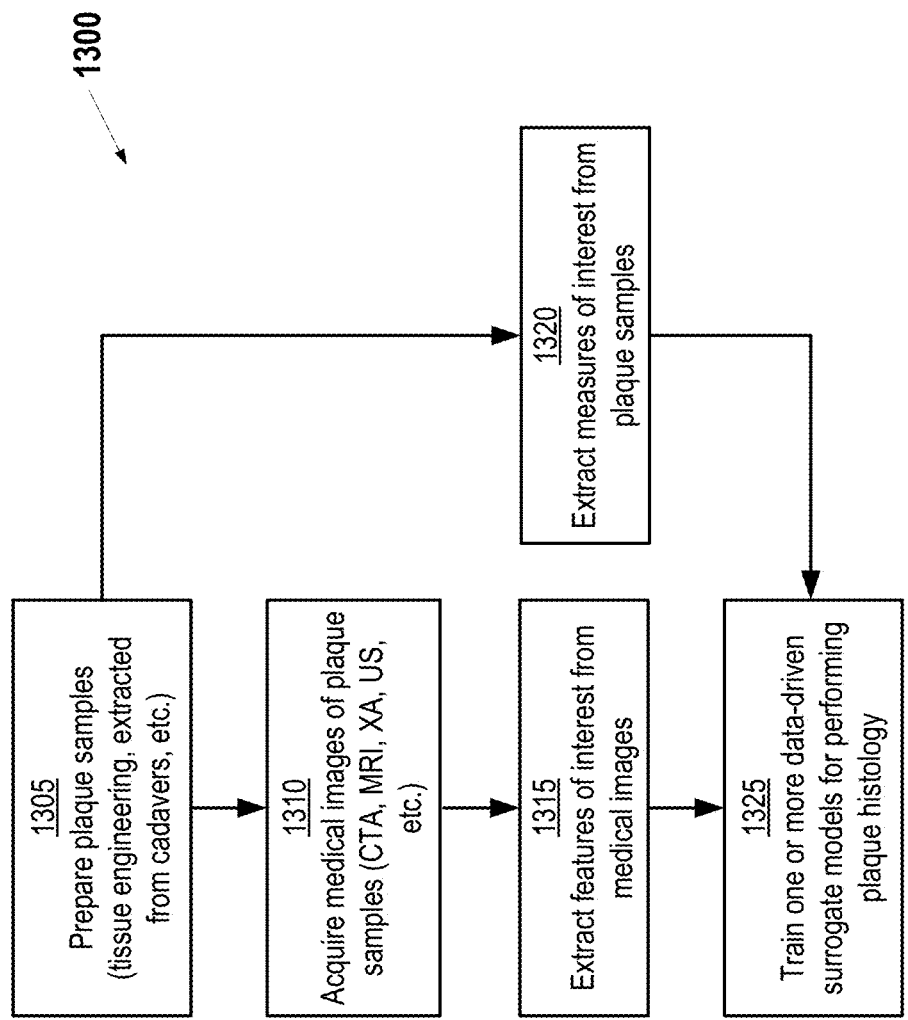
FIG. 13 presents a workflow for training an ML model to perform image-based plaque histology, according to some embodiments.

FIG. 13 shows a workflow 1300 for training an ML model to perform image-based plaque histology. At step 1305, plaque samples are prepared. These may be obtained either through tissue engineering, cadaver extractions, endarterectomy (e.g. carotid), etc. At step 1310, medical images of the plaque samples are acquired using any available medical imaging technologies (CTA, MRI, XA, US, etc.). At step 1320, the measures of interest are extracted based on the plaque samples (i.e. plaque histology is performed). At step 1315, plaque related features of interest are extracted from the acquired medical images. These features may include, without limitation, grayscale values in different parts of the image, grayscale values of neighboring regions, etc. Furthermore, in some embodiments, arterial wall strain may be used as a feature related to plaque composition (low strain—fibrous tissue; large strain—lipid tissue). Then, at step 1325, one or more ML models are trained to perform plaque histology based on the medical images.

Such ML models would be able to compensate for example for the blooming artifacts present on a CTA image in case of calcified plaque. Radiogenomics features may also be employed in the ML workflow (imaging biomarkers that are linked with the genomics of a pathology). In a different embodiment, plaque related data acquired through intravascular medical imaging technologies (IVUS, OCT, etc.) may be used for determining the ground truth values of the measures of interest. For example, a set of patients may be investigated both through CTA and IVUS. IVUS-based virtual histology may be used to determine the main constituents of each plaque and then used to train the aforementioned ML models.

In a different embodiment, a modified version of the workflow 1100 displayed in FIG. 11 may be employed to perform image-based plaque histology. For example, a non-linear dynamical systems discovery method may be used to derive the governing equations of medical image generation (using either in vitro studies—real tissue samples, or virtual histology studies). Then, derived governing equations may then be used to generate a large number of pairs of synthetic plaque compositions and corresponding synthetic images. Finally, the ML models discussed with respect to FIG. 11 can be trained for performing image based plaque histology.

Figure 14:
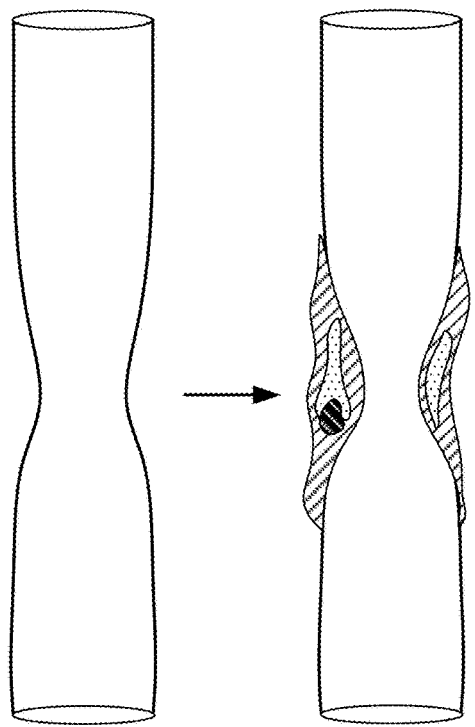
FIG. 14 shows a workflow for training ML models for identifying plaques on medical images, according to some embodiments.
Figure 14:
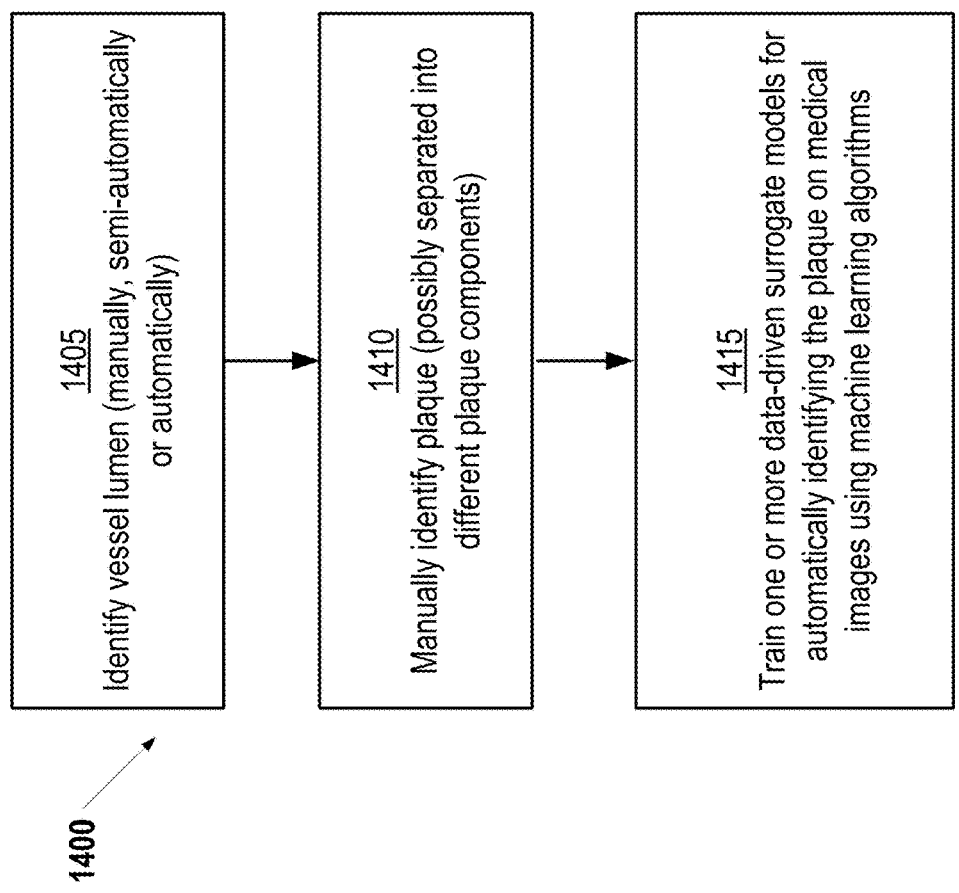

In another embodiment, ML models may be used to identify plaques on the medical images (and possibly also the plaque composition). For example, FIG. 14 displays on the left a workflow 1400 for training one or more ML models for identifying plaques on medical images. Starting from a large database with medical images of vessels, at step 1405, vessel lumen is identified on images. This may be performed automatically, semi-automatically or fully automatically. Next, at step 1410, plaque is manually identified (segmented) on the images. The plaques may be associated with vessel narrowings (as displayed in the right hand portion of FIG. 14) or not. Step 1410 may involve, for example, drawing of contours, identifying a set of points on the boundary of the plaque (of the different plaque constituents), etc. Then, at step 1415, one or more ML models are trained to identify the plaques on medical images. The first two steps may also be performed simultaneously in some embodiments. Advanced learning techniques like reinforcement learning may be combined with deep learning techniques to specifically learn based from the actions performed by the user while manually identifying/segmenting the plaque.

Figure 15:
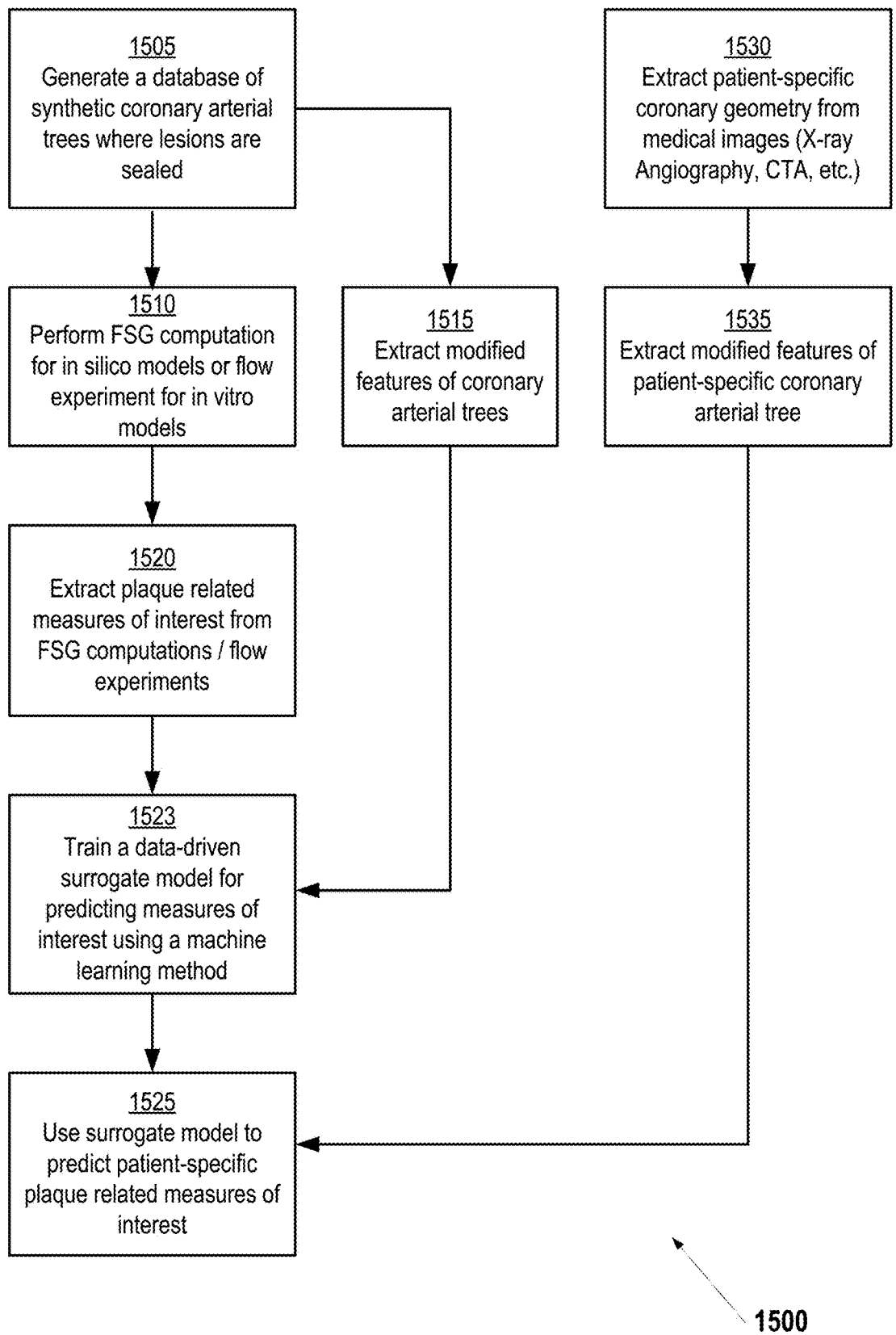
FIG. 15 shows a workflow for performing individual lesion assessment, according to some embodiments.

An ML algorithm may also be used to identify vulnerable lesions (which may or may not be flow-limiting). FIG. 15 illustrates a workflow 1500 for performing individual lesion assessment. In this workflow 1500, the vulnerable lesions are automatically identified and virtually sealed. The algorithm used for assessing the plaque related measures of interest is adapted so as to remove the effect of the vulnerable lesions on the hemodynamics and the future evolution of the anatomical model (in this case the initial geometry does not have to be modified).

Starting at step 1505 of FIG. 15, a database of synthetic coronary arterial trees where lesions are sealed is generated. Next, at step 1510, FSG computation is performed for in silico models or flow experiment for in vitro models. At steps 1515 and 1520, respectively, modified features of coronary arterial trees are extracted from the database and plaque related measures of interest are extracted from FSG computations/flow experiments. Then, at step 1523, a data-driven surrogate model is trained for predicting measures of interest using a machine learning method.

Continuing with reference to FIG. 15, at step 1530, a patient-specific coronary geometry is extracted from medical images (X-ray Angiography, CTA, etc.). Next, at step 1535 modified features of a patient-specific coronary arterial tree are extracted. For example, one approach would comprise modifying the features related to the growth of the plaque. Then, at step 1525 the surrogate model is used to predict patient-specific plaque related measures of interest. Similar algorithms/workflows may be used in case of device therapies (such as stenting, grafting etc.), whereas the measure of interest could be the viability/effectiveness of the device in the wake of plaque and/or thrombus initiation and growth.

Another important application in the context of atherosclerotic plaque is drug-based therapy planning. The typically prescribed drugs for treating atherosclerosis include statins (decrease the level of LDL cholesterol); fibrates (decrease the level of triglyceride); nicotinic acid (reduce both triglycerides and LDL); ezetimibe (decrease the level of cholesterol absorption in the digestive system; bile acid sequestrants (decreases bile acid level, which in turn increases cholesterol usage, leading to lower cholesterol level); and anti-inflammatory interleukin (IL)-13 (induce plaque stability).

Figure 16:
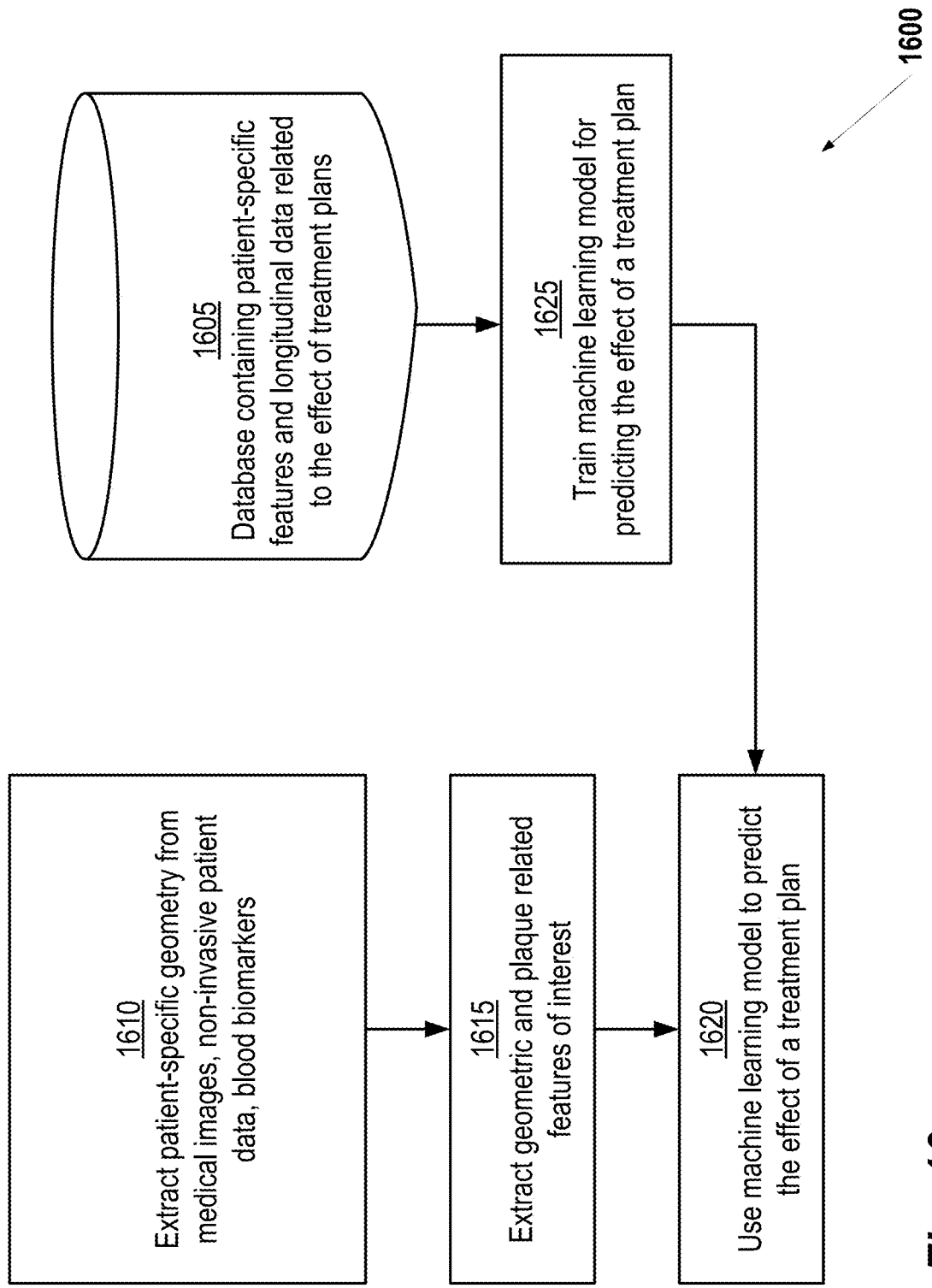
FIG. 16 presents an ML based workflow for predicting the effect of a treatment plan, according to some embodiments.

An ML based workflow may be used to estimate the effect of different drug based treatment plans and chose the best possible treatment plan for each patient as shown in the workflow 1600 presented in FIG. 16. A key element for this workflow 1600 is the existence of a database 1605 containing longitudinal data related to different treatment plans for various patients. This may be generated, for example, based on data acquired at different time points. This database is used at step 1625 to train an ML model to predict the effect of a treatment plan.

Continuing with reference to FIG. 16, at step 1610, patient-specific geometry is extracted from medical images (XA, CT, MRI, etc.), non-invasive patient data (demographics, patient history, etc.), and blood biomarkers. Next, at step 1615, geometric and plaque related features of interest are extracted from the patient-specific geometry. Finally, at step 1620, the trained ML model is used to predict the effect of a treatment plan based on the geometric and plaque related features of interest.

Separate ML models may be trained for different drugs (statins, fibrates, niacin, ezetimibe, bile acid sequestrants); different combinations of drugs; assessing the effect of changes in treatment plans; patients which have already suffered cardiovascular events; and patients without cardiovascular events The outcome measures of interest predicted by the ML model may be an optimal treatment plan (e.g., which drug, which quantity, etc.), lowering plaque growth rate/stopping plaque growth, decrease of cardiovascular event risk, etc. Additionally, a cascaded ML approach may be used in some embodiments (e.g., as described above with reference to FIG. 6). The first ML model in the cascade may focus on the prediction of hemodynamic and plaque related measures of interest and the second ML model may focus on the prediction of the effect of the treatment plan.

Computed results can be visualized on the scanner, or on another device, such as an imaging workstation. All of the above mentioned measures of interest related to plaque may be visualized including, without limitation, risk of a cardiovascular event related to atherosclerotic plaque (single score or as a time-dependent curve); future screening date; plaque composition (e.g., absolute/relative values of plaque components in a plaque); plaque evolution related measures of interest (e.g., future size, shape, composition and location of plaques); formation, evolution, and rupture of plaque; in-stent restenosis related measures of interest (e.g., degree of restenosis, time of onset, etc.); lesions which require sealing; and therapy planning (e.g. effectiveness of a drug treatment, viability/effectiveness of a device in the wake of plaque and/or thrombus initiation and growth).

Figure 17:
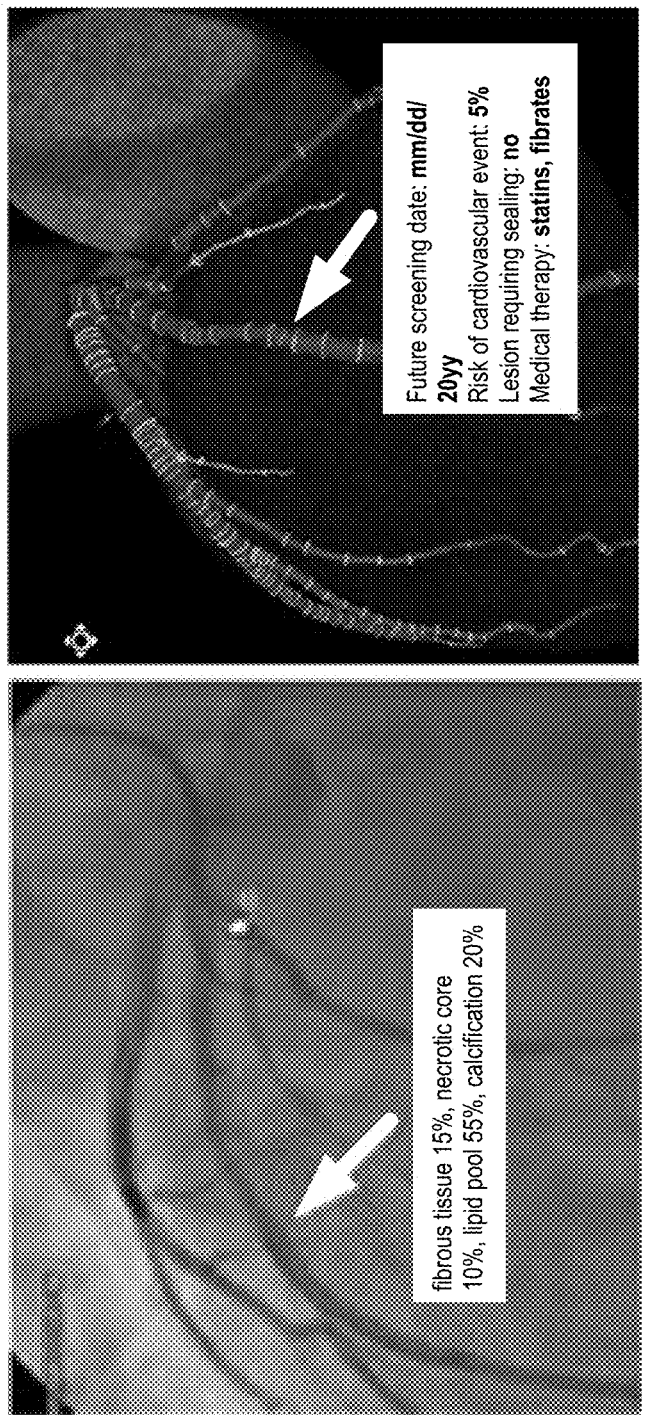
FIG. 17 shows examples of a tool to point and click points on an image, where the system visualizes the point and the associated measure of interest.

An example based on a coronary CTA image is displayed in FIG. 17. Any point on the image (related or not to a coronary plaque) can be queried (point & click) for the associated value of the measure of interest, and the corresponding value is shown overlaid to the image. As an example, points of interest/plaques can be selected and the corresponding plaque composition, future screening data, risk of cardiovascular event associated with the plaque, etc. can be displayed (FIG. 17). Alternatively, in some embodiments, the user can activate a "no click" mode, in which case the value of interest is displayed in correspondence of the cursor by just positioning the cursor on the position of interest. The system may provide a touch screen enabling interactions with the anatomical object of interest (e.g., gestures to rotate, zoom, pan, etc.). Point and touch functionality may cause the system to display the value of interest at the point of touch. Furthermore, the anatomical model of the vessels may be color-coded based on the values of the measure of interest (a continuous or a discrete color map may be used for this purpose). The above mentioned approaches may be used for a 3D or 2D visualization, which may be based on projections of the results on a plane.

When different modalities or multiple acquisitions from the same modality (one for feature extraction, another one for visualization) are used, registration of the images and features (spatial and temporal) is an important prerequisite. This can be done, for example, by specifying information of the image systems (in case they are registered), running algorithms on the images, or manually by the user by selecting land marks. When the same scanner is employed during examination and visualization, features can be table position, angulations, etc. If the measure of interest is a value representative for the entire anatomical model (e.g., risk of cardiovascular event/future screening date), this value may be displayed on a screen. The user may consider different treatment options, and the different outcomes may be displayed simultaneously on the screen/image so as to enable a fast evaluation of the different options. The visualization of plaque related measures of interest may be combined with the visualization of lesion specific diagnostic indices (e.g., coronary FFR). This may further inform the user with respect to which lesion should be treated.

Figure 18:
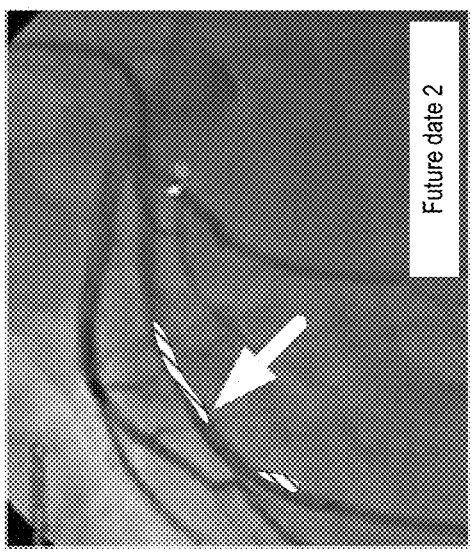
FIG. 18 provides an example visualization of coronary plaque at present and future dates.
Figure 18:
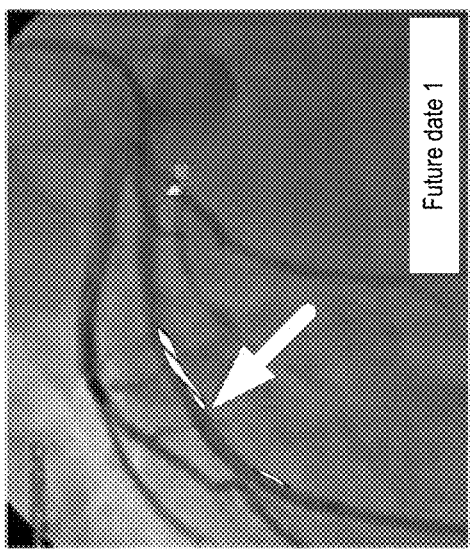
Figure 18:
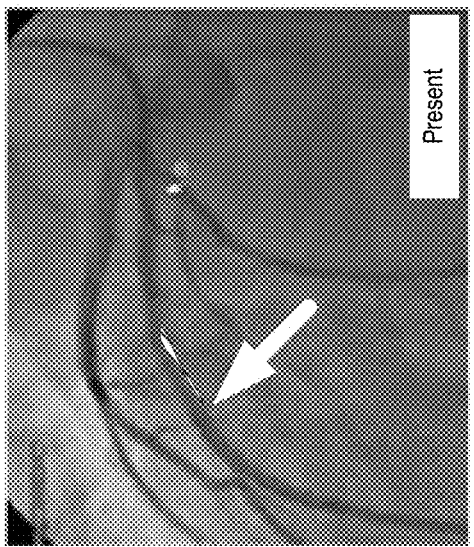

Another example is displayed in FIG. 18. Different images are generated for different future dates, whereas the predicted plaques and plaque sizes are displayed: the plaque size increases progressively, and also new plaques form.

Various additional features, enhancements, and other modification can be made to the learning-based generative methods described herein to provide additional extensions to the disclosed techniques. For example, in some embodiments, the learning-based generative methods may be used to also predict the formation of aneurysms, dissections, inflammation or other such disease of the vascular wall. In other embodiments, the methods may be used to also predict the formation of myocardial scar (due to insufficient oxygen supply), onset of angiogenesis, or the formation of tumors in various organs. Alternatively (or additionally), the learning-based generative methods may be made available as a service, which may be called by a hospital/clinician to obtain a patient-specific prediction related to the aspects mentioned above.

One advantage of ML models is that the online prediction is extremely fast; it outputs results almost instantaneously (in a matter of seconds). For example, they can be run directly on the workstation located at clinics/hospitals. However, there may be situations in which a hybrid on-site-off-site processing workflow may be required. For example, off-site processing can provide more detailed information or additional information that would not be available on-site, which is enabled by the less strict requirement on the processing time. Examples of such scenarios include employing a complex computational model available off-site but not on-site, providing different analyses or options as compared to the on-site processing (e.g., therapy planning may only be available off-site), etc. Similarly, on-site assessment may not be available at the time when the medical images are acquired. This may be due for instance to limitations of the imaging workstation (incompatible hardware or software configuration), or unavailability of the workstation providing the processing functionality. In this case, off-site processing can be offered as an alternative, to produce the same results as the on-site counterpart, or with the possibility of choosing different analyses or options.

Moreover, the on-site assessment can be inconclusive or uncertain due to intrinsic uncertainty of the quantity of interest. In this case, off-site processing can include consulting medical experts (human or databases) to find the best course of action, for instance based on previous clinical cases with similar characteristics. In another scenario, the on-site assessment provides a first approximation of the quantity of interest (for instance, not all image features can be extracted with confidence); in this case, off-site processing can include further image processing to extract more image features or with more confidence/less uncertainty. Off-site processing can also include evaluating a larger set of features (e.g., non-image features such as clinical history of the patient, risk factors for fractures, etc.) that can be incorporated in the predictor to improve the assessment. If the same type of data is available at different time points, the data acquired at the current time point may be analyzed on-site and then sent off-site for a comparative analysis with the previous acquisition. This may be used to determine the evolution of the pathology/patient so as to propose the optimal treatment strategy.

To implement off-site processing, a cloud-based computing environment may be used wherein a client device communicates with a server that hosts a highly efficient computing platform. In some embodiments, this computing platform provides parallel processing capabilities. One example of a parallel processing platform that may be utilized is illustrated below with respect to FIG. 19.

Additionally, in some embodiments, the workflows described herein can be implemented on a portable device (as an instance of wearable computing) and combined with wearable sensors for the online processing of acquired data. In other embodiments, a computing system implementing the workflows described herein may be combined with a personal assistant (e.g., Apple's SIRI), interacting with the individual in natural language (e.g., requesting the acquisition of data; or providing reminders for the actions mandated by the patient's health management plan; or providing feedback on user actions, such as a risk score for the assumption of particular foods or drinks).

As an additional supplement to the techniques described herein, once the models are executed and predictions are determined (e.g., regarding, patient outcome, suggestions for follow-up, etc.) a report can be automatically generated which presents all of the findings in a structured format (e.g., extensible markup language, Word document format, or Excel document format). The report can be part of the patient record in the hospital database.

Figure 19:
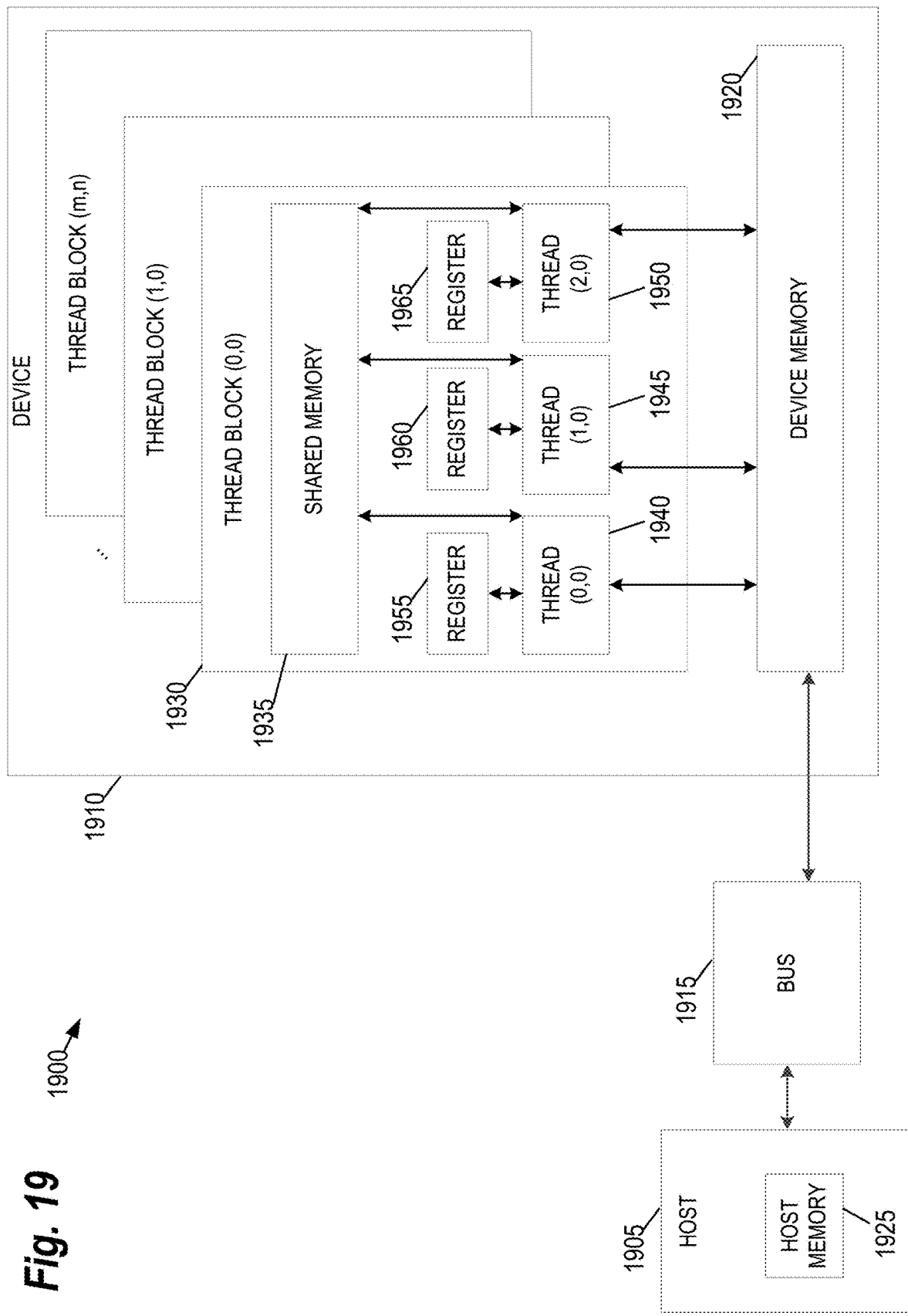
FIG. 19 provides an example of a parallel processing memory architecture that may be utilized to implement the ML models and other aspects of the various workflows discussed herein.

FIG. 19 provides an example of a parallel processing platform 1900 that may be utilized to implement the ML models and other aspects of the various workflows discussed herein. This platform 1900 may be used in embodiments of the present invention where NVIDIA CUDA™ (or a similar parallel computing platform) is used. The architecture includes a host computing unit ("host") 1905 and a graphics processing unit (GPU) device ("device") 1910 connected via a bus 1915 (e.g., a PCIe bus). The host 1905 includes the central processing unit, or "CPU" (not shown in FIG. 19), and host memory 1925 accessible to the CPU. The device 1910 includes the graphics processing unit (GPU) and its associated memory 1920, referred to herein as device memory. The device memory 1920 may include various types of memory, each optimized for different memory usages. For example, in some embodiments, the device memory includes global memory, constant memory, and texture memory.

Parallel portions of a big data platform and/or big simulation platform may be executed on the platform 1900 as "device kernels" or simply "kernels." A kernel comprises parameterized code configured to perform a particular function. The parallel computing platform is configured to execute these kernels in an optimal manner across the platform 1900 based on parameters, settings, and other selections provided by the user. Additionally, in some embodiments, the parallel computing platform may include additional functionality to allow for automatic processing of kernels in an optimal manner with minimal input provided by the user.

The processing required for each kernel is performed by a grid of thread blocks (described in greater detail below). Using concurrent kernel execution, streams, and synchronization with lightweight events, the platform 1900 of FIG. 19 (or similar architectures) may be used to parallelize portions of the model based operations performed in training or utilizing the workflows discussed herein. For example, in embodiments where a convolutional neural network is used as the ML model, the platform 1900 can be used to perform operations such as forward and backward convolution, pooling, normalization, etc. with the synthetic or patient-specific data.

The device 1910 includes one or more thread blocks 1930 which represent the computation unit of the device 1910. The term thread block refers to a group of threads that can cooperate via shared memory and synchronize their execution to coordinate memory accesses. For example, in FIG. 19, threads 1940, 1945 and 1950 operate in thread block 1930 and access shared memory 1935. Depending on the parallel computing platform used, thread blocks may be organized in a grid structure. A computation or series of computations may then be mapped onto this grid. For example, in embodiments utilizing CUDA, computations may be mapped on one-, two-, or three-dimensional grids. Each grid contains multiple thread blocks, and each thread block contains multiple threads. For example, in FIG. 19, the thread blocks 1930 are organized in a two dimensional grid structure with m+1 rows and n+1 columns. Generally, threads in different thread blocks of the same grid cannot communicate or synchronize with each other. However, thread blocks in the same grid can run on the same multiprocessor within the GPU at the same time. The number of threads in each thread block may be limited by hardware or software constraints.

Continuing with reference to FIG. 19, registers 1955, 1960, and 1965 represent the fast memory available to thread block 1930. Each register is only accessible by a single thread. Thus, for example, register 1955 may only be accessed by thread 1940. Conversely, shared memory is allocated per thread block, so all threads in the block have access to the same shared memory. Thus, shared memory 1935 is designed to be accessed, in parallel, by each thread 1940, 1945, and 1950 in thread block 1930. Threads can access data in shared memory 1935 loaded from device memory 1920 by other threads within the same thread block (e.g., thread block 1930). The device memory 1920 is accessed by all blocks of the grid and may be implemented using, for example, Dynamic Random-Access Memory (DRAM).

Each thread can have one or more levels of memory access. For example, in the platform 1900 of FIG. 19, each thread may have three levels of memory access. First, each thread 1940, 1945, 1950, can read and write to its corresponding registers 1955, 1960, and 1965. Registers provide the fastest memory access to threads because there are no synchronization issues and the register is generally located close to a multiprocessor executing the thread. Second, each thread 1940, 1945, 1950 in thread block 1930, may read and write data to the shared memory 1935 corresponding to that block 1930. Generally, the time required for a thread to access shared memory exceeds that of register access due to the need to synchronize access among all the threads in the thread block. However, like the registers in the thread block, the shared memory is typically located close to the multiprocessor executing the threads. The third level of memory access allows all threads on the device 1910 to read and/or write to the device memory. Device memory requires the longest time to access because access must be synchronized across the thread blocks operating on the device. Thus, in some embodiments, data can be divided into segments using data locality techniques generally known in the art. Then, each segment can be processed in parallel using register memory, with shared and device memory only being used as necessary to combine the results to provide the results for the complete dataset.

The embodiments of the present disclosure may be implemented with any combination of hardware and software. For example, aside from parallel processing architecture presented in FIG. 19, standard computing platforms (e.g., servers, desktop computer, etc.) may be specially configured to perform the techniques discussed herein. In addition, the embodiments of the present disclosure may be included in an article of manufacture (e.g., one or more computer program products) having, for example, computer-readable, non-transitory media. The media may have embodied therein computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

The invention claimed is:

1. A computer-implemented method for providing a personalized evaluation of assessment of atherosclerotic plaques for a patient, the method comprising:
   acquiring patient data comprising non-invasive patient data, medical images of the patient, and blood biomarkers;
   extracting features of interest from the patient data;
   training one or more machine learning models using a database of synthetic data comprising one or more of in silico anatomical models and in vitro anatomical models; and
   applying the one or more machine learning models to the features of interest to predict a plurality of measures of interest related to atherosclerotic plaque, wherein the plurality of measures of interest related to atherosclerotic plaque include a risk of cardiovascular event, plaque composition, plaque evolution, effect of a drug treatment, in-stent restenosis, lesions requiring sealing, indication of a future screening data, and effect of a device for therapy, wherein the risk of cardiovascular event includes coronary circulation, cerebral circulation, and peripheral circulation,
   wherein the one or more machine learning models are trained using a process comprising:
      performing fluid solid growth (FSG) computations for the in silico anatomical models or flow experiments for the in vitro anatomical models to yield output data;
      extracting measures of interest from the output data;
      extracting geometric features and plaque-related features from the database of synthetic data; and
      training the one or more machine learning models to predict measures of interest related to atherosclerotic plaque using the measures of interest from the output data, the geometric features, and the plaque-related features.

2. The method of claim 1, further comprising:
   generating a report in a structured format describing the measures of interest related to atherosclerotic plaque; and
   storing the report in a patient-specific medical record.

3. The method of claim 1, wherein the in silico anatomical models are generated by:
   initializing a new in silico anatomical model skeleton of a coronary arterial tree anatomical model by prescribing a number of vessels at each generation of the coronary arterial tree;
   defining healthy geometric information for each generation of the coronary arterial tree, wherein the healthy geometric information comprises one or more of vessel radius, a degree of tapering, and a branch length;
   establishing one or more stenoses in the coronary arterial tree which modify the healthy geometric information; and
   establishing plaque composition for each stenosis in the coronary arterial tree;
   updating the new in silico anatomical model based on the modified healthy geometric information and the plaque composition for each stenosis in the coronary arterial tree; and storing the new in silico anatomical model in the database of synthetic data.

4. The method of claim 3, wherein the plaque composition for each stenosis is established by randomly selecting a particular plaque composition from a plurality of predefined plaque composition types.

5. The method of claim 4, wherein the plaque composition for each stenosis comprises a plaque material established by:
   randomly selecting a center of each volume of plaque material;
   randomly selecting a size and a shape for the plaque material; and
   randomly selecting material proprieties for the plaque composition; and establishing the plaque material using the center, size, shape, and material properties.

6. The method of claim 4, wherein the plaque composition for each stenosis mimics a predefined high risk plaque composition.

7. The method of claim 1, wherein the one or more machine learning models comprise:
- a first machine model trained to predict plaque formation,
- a second machine model trained to predict plaque development, and
- a third machine model trained to predict plaque rupture.

8. The method of claim 1, wherein the machine learning models are applied in parallel to the features of interest.

9. The method of claim 1, wherein the one or more machine learning models comprise:
- a first machine learning model trained to predict an ischemic weight of each branch;
- a second machine learning model trained to predict ischemic contribution scores,
- a third machine learning model trained to predict hemodynamic measures of interest,
- a fourth machine learning model trained to predict plaque related measures of interest, and
- a fifth machine learning model trained to predict a risk of future cardiovascular event.

10. The method of claim 9, wherein the machine learning models are applied in a cascaded workflow that sequentially applies the machine learning models using outputs of each machine learning model as inputs for a subsequent machine learning model in the cascaded workflow.

11. The method of claim 1, further comprising:
generating a visualization of the measures of interest related to atherosclerotic plaque.

12. The method of claim 11, wherein the visualization comprises a coronary artery image and the method further comprises:
- receiving a user selection of a location within the coronary artery image; and
- in response to the user selection, presenting a measure of interest corresponding to the location in the visualization.

13. A computer-implemented method for training a machine learning model to provide a personalized evaluation of assessment of atherosclerotic plaques for a patient, the method comprising:
generating a database of synthetic data comprising one or more of in silico anatomical models;
performing fluid solid growth (FSG) computations for the in silico anatomical models to yield output data;
extracting measures of interest from the output data, wherein the measures of interest include a risk of cardiovascular event, plaque composition, plaque evolution, effect of a drug treatment, in-stent restenosis, and lesions requiring sealing;
extracting geometric features of the in silico anatomical models and plaque-related features from the database of synthetic data, wherein the plaque-related features include features describing likelihood of plaque development at a particular location, features describing growth speed of the plaque, wherein the plaque-related features are defined based on features describing likelihood of a rupture of the plaque and features describing likelihood of thrombus formation of a plaque surface; and
training one or more machine learning models to generate predicted measurements related to atherosclerotic plaque based on the geometric features of the in silico anatomical models trees and the plaque-related features.

14. The method of claim 13, further comprising:
applying the one or more machine learning models to the features of interest to generate predicted measurements related to atherosclerotic plaque.

15. The method of claim 14, further comprising:
receiving patient-specific measurements related to atherosclerotic plaque;
comparing the patient-specific measurements related to atherosclerotic plaque to the predicted measurements related to atherosclerotic plaque;
if the patient-specific measurements do not match the predicted measurements, retaining the one or more machine learning models using the patient-specific measurements.

16. The method of claim 13, further comprising:
receiving a specification of input uncertainties associated with each of the one or more of in silico anatomical models;
determining a confidence interval for each of the measures of interest;
using the confidence interval and the in silico anatomical models to train the one or more machine learning models to predict confidence intervals of the predicted measurements related to atherosclerotic plaque based on geometric features of anatomical models.

* * * * *